(12) United States Patent
Rege et al.

(10) Patent No.: US 11,896,724 B2
(45) Date of Patent: Feb. 13, 2024

(54) BIOACTIVE POLYMERIC DRESSING FOR ACCELERATED WOUND CLOSURE

(71) Applicant: Arizona Board of Regents on behalf of Arizona State University, Scottsdale, AZ (US)

(72) Inventors: Kaushal Rege, Chandler, AZ (US); Deepanjan Ghosh, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 668 days.

(21) Appl. No.: 17/065,283

(22) Filed: Oct. 7, 2020

(65) Prior Publication Data

US 2021/0100927 A1    Apr. 8, 2021

Related U.S. Application Data

(60) Provisional application No. 62/911,859, filed on Oct. 7, 2019.

(51) Int. Cl.

| | | |
|---|---|---|
| *A61K 33/242* | (2019.01) | |
| *A61N 5/067* | (2006.01) | |
| *A61L 15/18* | (2006.01) | |
| *A61L 15/44* | (2006.01) | |
| *A61L 15/20* | (2006.01) | |
| *A61L 15/32* | (2006.01) | |
| *A61K 38/39* | (2006.01) | |
| *A61P 17/02* | (2006.01) | |
| *A61N 5/06* | (2006.01) | |
| *A61K 31/417* | (2006.01) | |
| *A61K 9/70* | (2006.01) | |
| *A61K 38/18* | (2006.01) | |
| *A61L 26/00* | (2006.01) | |

(52) U.S. Cl.
CPC ............ *A61L 15/44* (2013.01); *A61K 9/7007* (2013.01); *A61K 31/417* (2013.01); *A61K 33/242* (2019.01); *A61K 38/1825* (2013.01); *A61K 38/39* (2013.01); *A61L 15/18* (2013.01); *A61L 15/20* (2013.01); *A61L 15/32* (2013.01); *A61L 26/0004* (2013.01); *A61L 26/008* (2013.01); *A61L 26/0066* (2013.01); *A61L 26/0095* (2013.01); *A61N 5/0616* (2013.01); *A61P 17/02* (2018.01); *A61L 2300/102* (2013.01); *A61L 2300/414* (2013.01); *A61L 2300/426* (2013.01); *A61L 2300/45* (2013.01); *A61N 5/067* (2021.08)

(58) Field of Classification Search
CPC .......... A61K 33/242; A61N 2005/0659; A61N 2005/066; A61N 5/0616; A61N 5/067; A61L 15/18; A61L 26/0004; A61L 26/0095; A61L 2300/102; A61L 15/44; A61L 26/0066; A61L 26/008; A61L 2300/414; A61L 2300/426; A61L 2300/04
See application file for complete search history.

(56) References Cited

U.S. PATENT DOCUMENTS

| | | | | |
|---|---|---|---|---|
| 5,804,213 A | * | 9/1998 | Rolf | A61L 26/0066 |
| | | | | 514/928 |
| 5,981,606 A | * | 11/1999 | Martin | A61Q 11/00 |
| | | | | 514/724 |
| 2008/0215020 A1 | * | 9/2008 | Reeves | A61M 1/916 |
| | | | | 604/305 |
| 2010/0172958 A1 | * | 7/2010 | Lucchesi | A61L 15/28 |
| | | | | 424/445 |
| 2011/0033503 A1 | * | 2/2011 | Sinko | A61L 15/44 |
| | | | | 514/420 |
| 2012/0276163 A1 | * | 11/2012 | Tselepis | A61K 9/205 |
| | | | | 536/3 |
| 2016/0050916 A1 | * | 2/2016 | Bellido-Gonzalez | |
| | | | | A61L 31/16 |
| | | | | 427/532 |
| 2016/0331594 A1 | | 11/2016 | Mumby et al. | |
| 2017/0100506 A1 | * | 4/2017 | Yuan | A61L 26/0047 |
| 2017/0232157 A1 | | 8/2017 | Rege et al. | |
| 2018/0110726 A1 | * | 4/2018 | Yu | A61K 47/38 |

(Continued)

FOREIGN PATENT DOCUMENTS

WO    2018200372    11/2018

OTHER PUBLICATIONS

Kim et al. Accelerated healing of cutaneous wounds using phytochemically stabilized gold nanoparticle deposited hydrocolloid membranes. Biomaterials Science. 2015, vol. 3, pp. 509-519. (Year: 2015).*

(Continued)

*Primary Examiner* — Jeffrey E. Russel
(74) *Attorney, Agent, or Firm* — Riverside Law LLP

(57) ABSTRACT

A wound dressing includes: a structural material formed into a dressing; at least one immunomodulatory agent associated with the dressing; and a growth factor associated with the dressing. A wound dressing kit includes: a structural material formed into a wound dressing; an immunomodulatory agent; and a growth factor composition, wherein the structural material contains the immunomodulatory agent and/or the immunomodulatory agent in a separate composition. A method of treating a wound in a tissue includes: applying an immunomodulatory agent to the wound; applying a wound dressing to the wound; and allowing the wound to heal with the immunomodulatory agent and wound dressing. The application of a growth factor can be before, during and/or after applying the wound dressing to the wound.

15 Claims, 17 Drawing Sheets

(56) References Cited

U.S. PATENT DOCUMENTS

2021/0213170 A1* 7/2021 Taboas ................ A61L 27/3847
2022/0218878 A1* 7/2022 Rai ...................... A61N 5/0625

OTHER PUBLICATIONS

Abdelgawad, A.M., S.M. Hudson, and O.J. Rojas, Antimicrobial wound dressing nanofiber mats from multicomponent (chitosan/silver-NPs/polyvinyl alcohol) systems. Carbohydr Polym, 2014. 100: p. 166-78.

Annabi, N., et al., Elastic sealants for surgical applications. Eur J Pharm 10 Biopharm, 2015. 95(Pt A): p. 27-39.

Bass, L.S. and M.R. Treat, Laser tissue welding: a comprehensive review of current and future clinical applications. Lasers Surg Med, 1995. 17(4): p. 315-49.

Boonkaew, B., et al., Antimicrobial efficacy of a novel silver hydrogel dressing 20 compared to two common silver burn wound dressings: Acticoat and PolyMem Silver((R)). Burns, 2014. 40(1): p. 89-96.

Bouten, P.J.M., et al., The chemistry of tissue adhesive materials. Progress in Polymer Science, 2014. 39(7): p. 1375-1405.

Kupietzky, A., and F. Levi-Schaffer. "The role of mast cell-derived histamine in the closure of an in vitro wound." Inflammation research 45.4 (1996): 176-180.

Lloyd, J.D., M.J. Marque, and R.F. Kacprowicz, Closure techniques. Emergency Medicine Clinics of North America, 2007. 25(1): p. 73.

Malone-Povolny, M. J., Maloney, S. E., & Schoenfisch, M. H. (2019). Nitric Oxide Therapy for Diabetic Wound Healing. Advanced healthcare materials, 1801210.

Numata, Yukikazu, et al. "The accelerating effect of histamine on the cutaneous wound-healing process through the action of basic fibroblast growth factor." Journal of Investigative Dermatology 126.6 (2006): 1403-1409.

Russell Urie, S.Q., Michael Jaffe, and Kaushal Rege., Gold Nanorod-Collagen Nanocomposites as Photothermal Nanosolders for Laser Welding of Ruptured Porcine Intestines. ACS Biomater. Sci. Eng, 2015. 1: p. 805-815.

Talmor, M., Clifford B. Bleustein, and Dix P. Poppas., laser tissue welding: a biotechnological advance for the future. Archives of facial plastic surgery, 2001. 3: p. 15 207-213.

Urie et al., "Rapid Soft Tissue Approximation and Repair Using Laser-Activated Silk Nanosealants." Adv. Func. Mat. 2018; 28 (42), 1802874.

Wharram, Scott E., et al. "Electrospun silk material systems for wound healing." Macromolecular bioscience 10.3 (2010): 246-257.

Xie, J., et al., Silver nanoplates: from biological to biomimetic synthesis. ACS Nano, 2007. 1(5): p. 429-39.

Yeboah, Agnes, et al. "Stromal cell-derived growth factor-1 alpha-elastin like peptide fusion protein promotes cell migration and revascularization of experimental wounds in diabetic mice." Advances in wound care 6.1 (2017): 10-22.

Zhang, Wei, et al. "Silk fibroin biomaterial shows safe and effective wound healing in animal models and a randomized controlled clinical trial." Advanced healthcare materials 6.10 (2017): 1700121.

* cited by examiner

BIOACTIVE POLYMERIC DRESSING FOR ACCELERATED WOUND CLOSURE

CROSS-REFERENCE TO RELATED APPLICATIONS

This patent application claims priority to U.S. Provisional Application No. 62/911,859 filed Oct. 7, 2019, which provisional is incorporated herein by specific reference in its entirety.

GOVERNMENT RIGHTS

This invention was made with government support under R01 EB020690 awarded by the National Institutes of Health. The government has certain rights in the invention.

BACKGROUND

Surgical repair of wounds or openings in body tissues using sutures, bandages, dressings, skin equivalents, tissue glues, or other closure means are longstanding treatments that have changed very little in recent years. However, sutures and other closure means may not be suitable for use in friable tissue or other tissues or wound types that are difficult to close, such as ranging from acute wounds (e.g., stabbing, surgical, etc.) to chronic slow healing wounds (e.g., diabetes wound). Also, prior wound healing techniques have not overcome some of the difficulties experienced by difficult or slow healing wounds.

Slow healing and chronic non-healing wounds cost the US healthcare system over $25 billion a year. Such wounds are a common complication of diabetes, but may persist without significant healing for a variety of reasons. Compared to non-diabetic wounds, diabetic wounds take longer to heal, which can lead to the development of chronic wounds that can significantly worsen outcomes in patients.

Current methods for chronic wound care (e.g., for diabetic wounds or other long-term wounds) include topical antibiotics, dressings, growth factor injections, and skin substitutes. However, these methods are often either costly or fail to achieve proper healing. For decades, conventional wisdom has pointed to growth factors as the main driving force of wound healing; thus, growth factors have become the center of therapeutic developments. Becaplermin (recombinant human PDGF-BB) is an example of a FDA-approved growth factor therapy, but it only shows modest efficacy, is costly, and has the potential to cause cancer in patients.

Laser tissue welding is a platform technology that has been researched for wound closing. In laser tissue welding, an exposed chromophore converts laser light to heat to rapidly seal tissue wounds or incisions. With the use of exogenous chromophores in laser tissue welding materials, laser irradiation can be employed at wavelengths of 650-1350 nm; however, tissue absorbance at this wavelength is lowest for light in the near infrared range (700-1000 nm wavelength).

General current state of the art in sutures/other closure methods can include the following types and associated issues. Triclosan-coated sutures are basic sutures (e.g., traumatic and must puncture the tissue multiple times) and can have leakage or dehiscence, and the sutures do not integrate with the tissue. Staples require removal; can have leakage, trauma, and inflammation; and may result in greater scarring. Fibrin glue is brittle when cured, may cause problems with sequestering of bacteria, and is not suitable for internal applications. Sealants and adhesives require curing times, which can be long or require a UV light that may be harmful to cells, and typically are used over a sutured closure, and thereby are not standalone products. Albumin solder and other solders for laser tissue welding are liquid systems with inconsistent reproducibility, and they use organic dyes as a chromophore within a liquid, which results in rapid loss of chromophore stability due to photobleaching, and also results in leaching of the chromophore to surrounding tissue, which is not beneficial.

Dressings and skin equivalents offer suitable coverings, but may have drawbacks ranging from sequestering bacteria to inhibiting healing to being problematic by integrating with the wound when not biodegradable. However, biodegradable dressings may be configured to integrate with a wound, and may be of natural or synthetic polymer material. Skin grafts continue to be developed.

Wound repair continues to be a surgical necessity, and research into improved wound repair is desirable. Therefore, it would be advantageous to have a system for improving surgical repair of wounds that can overcome the limitations of traditional closure means.

SUMMARY

In some embodiments, a wound dressing can include: a structural material formed into a dressing, wherein the structural material ranges from about 2-25 wt %; at least one immunomodulatory agent associated with the dressing; and a growth factor associated with the dressing. In some aspects, the structural material is biodegradable and/or bioabsorbable. In some aspects, the structural material is a natural substance, a synthetic substance, or a natural substance that has been chemically modified. In some aspects, the immunomodulatory agent is selected from the group of histamine, histamine receptor agonists, monocyte chemoattractant protein-1 (MCP1), antibodies, 2-pyridylethylamine, histamine—trifluoromethyl—toluidine dimaleate (HTMT), diphenhydramine, terfenadine, dimaprit, cimetidine, ranitidine, Na-methylhistamine, azomethine prodrug of (R)-α-methylhistamine, impentamine, clobenpropit, immepip, imetit, 4-Methylhistamine and combinations thereof. In some aspects, the growth factor is selected from the group of stromal cell-derived factor (SDF1), basic fibroblast growth factor (bFGF), transforming growth factor (TGF), epidermal growth factor (EGF), keratinocyte growth factor (KGF), vascular endothelial growth factor (VEGF), heat shock protein 90 alpha (HSP90α), F5 subunit of heat shock protein 90 alpha (HSP90α), each optionally fused with elastin-like polypeptide (ELP), and combinations thereof. In some aspects, gold particles are included in the structural material. In some aspects, the growth factor is associated with the gold particles. In some aspects, the structural material includes a laser stimulated material that is stimulated by near IR laser light of about 650 nm to about 1400 nm.

In some embodiments, a wound dressing kit can include: a structural material formed into a wound dressing; an immunomodulatory agent; and a growth factor composition, wherein the structural material contains the immunomodulatory agent and/or the immunomodulatory agent is in a separate composition. In some aspects, the immunomodulatory agent is a separate composition. In some embodiment, the kit includes treatment instructions that define an administration protocol for the growth factor composition. In some aspects, the administration protocol recites that the growth factor composition is applied to a wound at a defined time period after application of the wound dressing to the wound.

In some embodiments, a method of treating a wound in a tissue can include: applying an immunomodulatory agent to the wound; applying a wound dressing to the wound; and allowing the wound to heal with the immunomodulatory agent and wound dressing. In some aspects, the method includes applying a growth factor to the wound before, during and/or after applying the wound dressing to the wound. In some aspects, the wound dressing includes the immunomodulatory agent and application of the wound dressing to the wound applies the immunomodulatory agent to the wound. In some aspects, the immunomodulatory agent is in a separate composition from the wound dressing, wherein the immunomodulatory agent is applied to the wound before applying the wound dressing to the wound. In some aspects, the method can include: irradiating the wound through the wound dressing with at least one laser light having a wavelength of about 700 nm to about 1400 nm, or about 800 nm.

In some embodiments, the method is devoid of using a suture, staple, clamp, or other structural element with the wound dressing to treat the wound. In some embodiments, the method includes using a suture, staple, clamp, or other structural element with the wound dressing to fasten the wound dressing to the tissue.

In some embodiments, a wound treatment method includes: removing the wound dressing from the wound; and applying a second wound dressing to the wound with or without applying a second administration of immunomodulatory agent and/or growth factor to the wound.

In some embodiments, the method can include applying a second histamine composition and/or growth factor composition to the wound without removing the wound dressing from the wound.

In some embodiments, the method is performed with a subject that has diabetes. As such, the methods can be used to treat diabetic skin wounds or other diabetic wounds.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
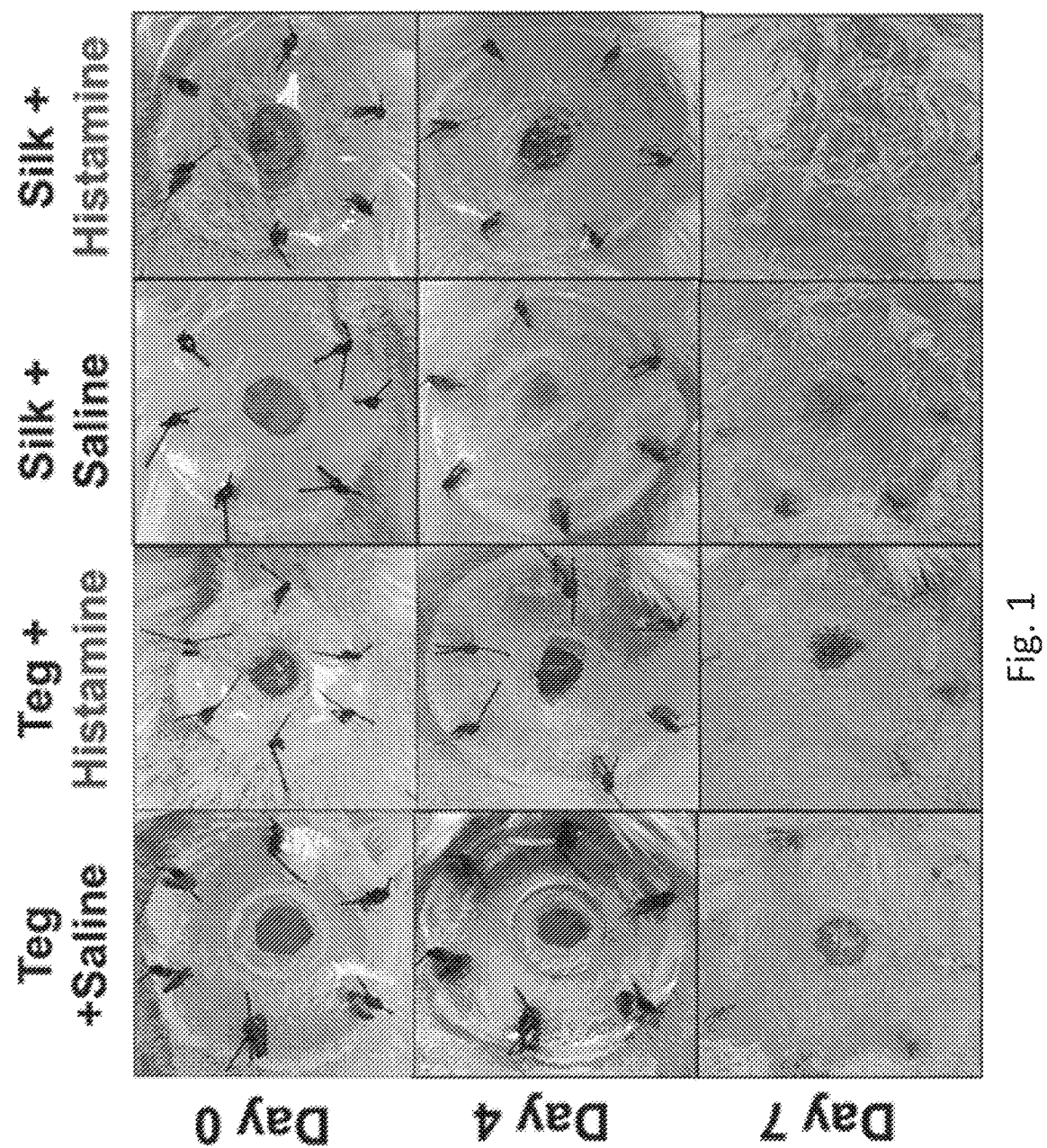
FIG. 1 includes images of a wound closure procedure, which was performed with BALB/c mice (about 8-10 weeks old), with a wound size of about 5 mm (n=10), and with a histamine concentration of 3.4 mg/kg per mouse.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes a bioactive dressing material with an immunomodulatory agent that can cooperatively facilitate improved wound healing. The bioactive dressing material can be any suitable natural polymer or synthetic polymer, or derivative thereof whether biostable or biodegradable. Examples of suitable bioactive dressing materials and immunomodulatory agents are provided herein. The bioactive dressing material can be used in facilitating closure of a wound, and can be used in wounds of various depths, lengths, and surface area. Thus, this technology pertains to the field of wound healing, photothermal approaches of wound healing/tissue repair, and immunomodulatory approaches for accelerated wound closure.

In some embodiments, the present technology can include the use of a growth factor along with the bioactive dressing material and the immunomodulatory agent. The addition of the growth factor can improve the healing function of the dressing. The growth factor can be associated with a polypeptide or nanoparticle for improve delivery, such as controlled delivery, and improved availability of the growth factor at the site of the wound. In some aspects, the treatment includes the combination of the bioactive dressing, immunomodulatory agent, and growth factor. However, some embodiments may specifically exclude the use of a growth factor with the bioactive wound dressing and immunomodulatory agent at the time of application of the dressing. The growth factor can be administered at some time after application of the dressing.

In some embodiments, the present technology can include the use of an immunomodulatory agent that can be used for modulating an immune response, which can be beneficial for the would dressing. The immunomodulatory agent can be a histamine receptor agonist, such as histamine. As part of an immune response to foreign pathogens, histamine is produced by basophils and by mast cells found in nearby connective tissues. Histamine increases the permeability of the capillaries to white blood cells and some proteins, to allow them to engage pathogens in the infected tissues. Thus, the immunomodulatory agent can include histamine or functionally active equivalents, or other agents that are histamine receptor agonists.

In some embodiments, the wound dressing can include a structural material formed into a dressing, at least one immunomodulatory agent associated with the dressing; and a growth factor associated with the dressing. In some aspects, the structural material is biostable, such as when the dressing is temporary and replaceable, such as in a wound treatment. That is, the dressing is used for a time period, and then removed and optionally replaced with a subsequent dressing. In some aspects, the structural material is biodegradable and/or bioabsorbable. The ability of the material to degrade and disintegrate can be used for more permanent implant and/or surface covering wound treatments, where the material is implanted or covered over the wound and left to erode and/or integrate with the tissue. The additional therapeutic treatments, such as injection of growth factor can be performed after the dressing is applied. In some aspects, the structural material is a natural substance, a synthetic substance, or a natural substance that has been chemically modified, such as those described herein and equivalents. The growth factor can be injected through the wound dressing into the wound.

In some embodiments, the growth factor is on or in the structural material. In some embodiments, the growth factor is located within a biodegradable coating on the structure, which can be configured to delay release of the growth factor until a predetermined time point after application of the dressing. For example, the growth factor release delay can be 1, 2, 3, 4, 5, 6, or 7 days or longer after application of the dressing to the wound. In some aspects, the body of the structural material can include the growth factor and be biodegradable to slowly release the growth factor in a selective release profile, such as: continuously upon application to a wound; continuously after a delay upon application to a wound; as a bolus or short infusion upon application to a wound; as a bolus or short infusion after a delay upon application to a wound; increasing in amount over a time period; decreasing in amount over a time period; delay of release; or combinations thereof as well as other release profiles.

In some embodiments, the immunomodulatory agent is on or in the structural material. In some aspects, the immunomodulatory agent is coated on at least one surface of the dressing. The coating can include a coating carrier, such as another biodegradable material. In some aspects, the immunomodulatory agent is embedded within a body of the dressing. In some aspects, the body of the structural material can include the immunomodulatory agent and be biodegradable to slowly release the immunomodulatory agent in a selective release profile, such as: continuously upon application to a wound; continuously after a delay upon application to a wound; as a bolus or short infusion upon application to a wound; as a bolus or short infusion after a delay upon application to a wound; increasing in amount over a time period; decreasing in amount over a time period; delay of release; or combinations thereof as well as other release profiles. While the delivery of the immunomodulatory agent may be delayed, the data indicates providing the immunomodulatory agent upon application of the dressing. Thus, a simultaneous or shortly thereafter cooperative application of the dressing and administration of the immunomodulatory agent can be beneficial.

The wound dressing can be provided in various forms and shapes, such as those known for bandages and for topical coverings. The dressing can be formed into a sheet of the structural material. In some aspects, the dressing is a film, hydrogel, paste, or other polymeric body that can be applied directly to the wound.

In some embodiments, the immunomodulatory agent and/or growth factor is within or associated with a polypeptide, nanoparticle, microparticles, or liposome. In some aspects, the growth factor is within or associated with a polypeptide, which may be considered to be a nanoparticle. In some aspects, the growth factor can be applied to a nanoparticle to form growth factor nanoparticles (GFNPs). In some aspects, the growth factor can be linked to an polypeptide, such as an elastin-like polypeptide. In some aspects, the immunomodulatory agent is not provided with a polypeptide, nanoparticle, microparticles, or liposome.

In some embodiments, the bioactive dressing is a silk dressing made from silk fibroin (e.g., extracted from Bombyx mori silkworm cocoons). In other embodiments, the bioactive dressing can be made from any natural polymer (e.g., collagen, alginate, chitosan, hyaluronic acid, fibrin, cellulose, dextran or the like) or any synthetic polymer (e.g., PLGA, modified polyurethanes, or the like). The natural or synthetic polymer can be biodegradable in some instances, and biostable in other instances. Biodegradable materials can integrate with the wound, where biostable materials can stay separate and be removed from the wound.

Some examples of natural polymers that can be configured as dressing materials can include: structural tissue proteins, such as collagen or other structural proteins from skin or other connective tissues; polysaccharides, such as alginate, chitosan, chitin, agarose, or cellulose; extracellular matrix or connective tissue proteins, such as laminin or elastin; glycoproteins, such as fibronectin; glycosaminoglycans or any type, such as hyaluronic acid, whether sulfated or non-sulfated; fibrous proteins, such as fibrin, whether globular or non-globular; chemically modified structural tissue proteins, such as gelatin, which is from hydrolyzed collagen; or a protein fiber, such as silk; or combinations thereof.

In some embodiments, any type of collagen can be used for the dressing material. For example, the collagen can include: Type I collagen from skin, tendon, vasculature, organs, or bone; Type II collagen from cartilage; Type III collagen that is reticulate, such as from reticular fibers; Type IV collagen from basal lamina; Type V collagen from cell surfaces, hair, and placenta. The collagen can be completely natural or semi-natural if chemically processed or otherwise derivatized.

In some embodiments, any type of polysaccharide can be used for the dressing material. There are many different polysaccharides that can be used in the present technology. The substances can include polymeric carbohydrates that include chains of monosaccharides coupled through glycosidic linkages, and which may give monosaccharides or oligosaccharides upon hydrolysis or other cleavage. Example polysaccharides can include alginate, chitosan, chitin, agarose, cellulose; cellulose acetate, celluloid, nitrocellulose, starch, amylose, pectin, amylopectin, glycogen, callose, laminarin, chrysolaminarin, xylan, arabinoxylan, mannan, fucoidan, and galactomannan, combinations thereof, or others.

In some embodiments, the glycoprotein can include proteins with oligosaccharide chains (e.g., glycans) attached to amino acid side-chains. Examples can include fibronectin, mucins, immunoglobulins, gonadotropins, miraculin, or others.

In some embodiments, the glycosaminoglycans can include chondroitin sulfate, dermatin sulfate, keratin sulfate, heparin, heparin sulfate, hyaluronan, and others, In some embodiments, the fibrous proteins can include fibrin, actin, Arp2/3, coronin, dystrphin, elastin, F-spondin, fibronectin, keratin, myosin, nebulin, pikachurin, spectrin, tau, tinin, tropomyosin, tubulin, combinations thereof, or others.

In some embodiments, the structural fiber can be silk from any origin. The silk may be from any insect or arachnid or arthropod. Some examples include silk worms, webspinners, raspy crickets, bees, wasps, ants, silverfish, mayflies, thrips, leafhoppers, beetles, lacewings, fleas, flies, midges, or others.

In some embodiments, the dressing material can be a semi-natural polymer, which can be derived from any natural polymer, such as those described herein or otherwise known. For example, a semi-natural polymer can be obtained by chemically modifying or otherwise derivatizing a natural polymer. Semi-natural polymers can also include natural polymers, whether natural or chemically modified, having other substances contained therein. The substances can be fillers, crosslinkers, or other materials. In some aspects, the semi-natural polymer can include a light absorbing substance, which is not a light responsive particle (gold) or a pigment or dye.

In some embodiments, the dressing material can be a synthetic polymer. Examples of synthetic polymers that can be used as light absorbing materials can include poly(lactic acid), poly(glycolic acid), poly(lactic-glycolic acid), poly(vinyl alcohol), polyamide, polyurethane, poly(ethylene oxide), polyglyconate, poly(glycolic-caprolactone), polypropylene, polyethylene, poly(hydroxyl acid), polyhydroxyalkanoate, polyanhydride, poly(orthocarbonate), polycarbonate, polyphosphonate, silicones (e.g., polysiloxanes, such as polydimethyulsiloxane (PDMS) or others), combinations thereof, or others. The synthetic polymer can be biodegradable or biostable. "Biostable" denotes a high chemical stability of a compound in an aqueous environment, which is similar to the environment, found in the human body, such as, by way of example, and not limitation, phosphate buffered saline (pH 7.2). "Biodegradable polymer" denotes those polymers that degrade or hydrolyze inside the human or animal body without producing harmful degradation products. Poly(lactic acid) poly(lactide) (PLA) is a term used for a polymer which is made from lactide or lactic acid. Similarly, PGA is a term used for polyglycolic acid or polyglycolate. Such polymers are generally referred to as polylactones or polyhydroxy acids.

In some embodiments, the dressing material may be configured as a hydrogel. A "hydrogel" refers to a semisolid composition constituting a substantial amount of water, and in which polymers or mixtures thereof are dissolved or dispersed. The hydrogels may be physically or chemically crosslinked.

In some embodiments, the dressing material may include a crosslinker. For example, the crosslinker can be included with a natural polymer, semi-natural polymer, or synthetic polymer. The crosslinker can crosslink the material. "Crosslink" is defined as understood by those skilled in polymer chemistry art. In general, cross-linking refers to the method of forming covalent bonds or crosslinks between polymeric/macromolecular molecules. The crosslinking process also generally refers to a fixation process which stabilizes the tissue by making the tissue less antigenic and thus less susceptible to enzymatic degradation. A "crosslinking agent" is defined as a compound capable of forming the crosslinking. For example, glutaraldehyde is generally known in the art as a crosslinking agent for the tissue.

In some embodiments, the crosslinker can include poly (ethylene glycol) diglycidyl ether, glycerol diglycidyl ether, 1,4-butanediol diglycidyl ether, ethylene glycol glycidyl ether, polypropylene glycol diglycidyl ether, combinations thereof, or others.

The dressing materials can be liquid, gels, hydrogels, pastes, films, matrices, bandages, or other when applied to the wound. The components of the polymeric films are composed of but not limited to the following: natural polymers, such as collagen, alginate, chitosan, cellulose, laminin, fibronectin, elastin, hyaluronic acid, fibrin, gelatin, agarose, silk, or combinations thereof; synthetic polymers, such as poly(lactic acid), poly(glycolic acid), poly(lacticglycolic acid), silicones, poly(vinyl alcohol), polyamide, polyurethane, polyethylene oxide, or combinations thereof; and optionally crosslinkers, such as poly(ethylene glycol) diglycidyl ether, glycerol diglycidyl ether, 1,4-butanediol diglycidyl ether, ethylene glycol glycidyl ether, polypropylene glycol diglycidyl ether, or combinations thereof.

Some examples can include the structural material having silk, collagen, alginate, chitosan, hyaluronic acid, fibrin, cellulose, dextran nylon, rayon, polyethylene, pluronic F127, laminin, fibronectin, polyacrylamide, aminoglycoside hydrogels, poly-lactic acid, poly-glycolic acid, poly-lactic-co-glycolic acid, polyglyconate, polydioxanone, poly-glycolic-caprolactone, cotton, gelatin, polypropylene, polysulfone, copolymers thereof, or combinations thereof.

In some embodiments, the immunomodulatory agent can be a bioactive small molecule that can accelerate healing. Histamine is a small bioactive molecule that functions as an immunomodulatory agent, but a number of other immunomodulator molecules can be used along with the bioactive dressing. Here, the immunomodulators can be immunostimulators that stimulate the immune system similar to histamine. The immunostimulators can increase permeability of capillaries around the wound to white blood cells and some proteins to improve healing of the wound Immunostimulants can include colony stimulating factors (e.g., glycoproteins that promote production of white blood cells, such as filgrastim, pegfilgrastim, tbo-filgrastim, sargramostim), interferons (e.g., beta-1a, alfacon-1, gamma-ab, alfa-n3), interleukins (e.g., aldesleukin, oprelvekin), or others (e.g., glatiramer, pegademase bovine, plerixafor). The immunomodulatory agent can be selected for agonizing a histamine receptor, such as H1 or H2.

In some embodiments, the immunomodulatory agent can be a small molecule, peptide, or the like that modulates the immune system, where histamine or other similar types of immunomodulatory agents can be examples, such as histamine receptor agonists, MCP1, and histamine receptor antibodies, or others. Histamine receptor agonists can include betazole, impromidine, betahistine, or others.

In some embodiments, the immunomodulatory agent is selected from the group consisting of L-arginine, prostacyclin, prostaglandin D2, prostaglandin E2, bradykinin, heparin, Endothelium-derived hyperpolarizing factor (EDHF).

In some embodiments, the immunomodulatory agent is selected from the group of histamine, histamine receptor agonists, monocyte chemoattractant protein-1 (MCP1), antibodies for histamine receptor, 2-pyridylethylamine (H1R agonist), histamine—trifluoromethyl—toluidine dimaleate (HTMT) (H1R agonist), diphenhydramine (H1R antagonist), terfenadine (H1R antagonist), dimaprit (H2R agonist), cimetidine (H2R antagonist), ranitidine (H2R antagonist), Na-methylhistamine (H3R agonist), azomethine prodrug of (R)-α-methylhistamine (BP-2-94)(H3R agonist), impentamine (H3R agonist or antagonist), clobenpropit (H3R antagonist), immepip (4-(1H-imidazol-5-ylmethyl)piperidine; H4R agonist), imetit (2-(1H-imidazol-5-yl)ethyl carbamimidothioate; H4R agonist), 4-Methylhistamine (H4R agonist), and combinations thereof.

In some embodiments, the methods also deliver a growth factor to the wound. In some aspects, the growth factor includes a stromal cell-derived factor (SDF1), basic fibroblast growth factor (bFGF), transforming growth factor (TGF), epidermal growth factor (EGF), keratinocyte growth factor (KGF), vascular endothelial growth factor (VEGF), heat shock protein 90 alpha (HSP90α) or combinations thereof. In some aspects, the growth factor can include the growth factor linked to ELP. An example can be covalent linking, such as by being a fusion protein. The examples can include stromal cell-derived factor (SDF1-ELP), basic fibroblast growth factor (bFGF-ELP) or other growth factors that promote growth of tissue and/or skin. Additional examples can include transforming growth factor (TGF, or TGF-ELP), epidermal growth factor (EGF, or EGF-ELP), keratinocyte growth factor (KGF, KGF-ELP), vascular endothelial growth factor (VEGF, VEGF-ELP), heat shock protein 90 alpha (HSP90α, HSP90α-ELP) F5 subunit of heat shock protein 90 alpha (HSP90α), or others. The growth factors can be administered along with the bioactive dressing or at different time points during healing to further accelerate healing kinetics and improve the efficacy of the bioactive dressing. The growth factors can be fused with ELP (elastin-like polypeptide), included in nanoparticles, or embedded in a delivery matrix or gel. The growth factors can be linked to or included in nanoparticles. The thermal transition of ELP can also help with healing, such as when used with a laser.

In some embodiments, the growth factor is selected from the group consisting of platelet-derived growth factor (PDGF), Angiopoietin, Insulin-like growth factor (IGF), granulocyte-macrophage colony-stimulating factor (GM-CSF), Tumor necrosis factor-alpha (TNFα).

In some embodiments, the growth factor includes SDF1-ELP or FGF2-ELP, or a combination of growth factors that includes SDF1-ELP and FGF2-ELP.

The active substances, such as the immunomodulator agents or growth factors can be included in simple pharmaceutically acceptable carriers, or included in gels, pastes, microparticles, nanoparticles, or other drug delivery modalities, which can be configured for a more sustained release and delivery. An example can include the bioactive substances being encapsulated within liposomes.

In some embodiments, the amount of structural material in the wound dressing can range from about 2-25 wt %, were some examples include ranges from about 6-10 wt %, about 5-12 wt %, about 4-15 wt %, about 3-20 wt %, or about 2-25 wt % of the biocompatible structural material.

In some embodiments, the amount of immunomodulator agent in the wound dressing can range from about 5 mM-2 M, were some examples include ranges from about 10 mM-100 mM, about 5 mM-75 mM, about 80 mM-400 mM, about 250 mM-1 M, or about 750 mM-2 M of the biocompatible structural material.

In some embodiments, the amount of growth factor in the wound dressing can range from about 0.1 μM-100 μM, were some examples include ranges from about 0.5 μM-5 μM, about 0.1 μM-10 μM, about 1-25 μM, about 60 μM-100 μM, or about 15-75 μM of the biocompatible structural material.

In some embodiments, an example would dressing composition can include the following: structural material in an amount of about 8 wt % or from about 4 wt % to about 12 wt %; immunomodulatory agent in an amount of about 40 mM or about 20 mM to about 60 mM; and growth factor in an amount of about 2 μM or about 0.5 μM to about 4 μM.

In some embodiments, the immunomodulatory agent can be administered in an amount of about 0.2-20 mg/kg of the subject, or from about 0.5-2 mg/kg to about 0.2-1 mg/kg, or from about 1-7.5 mg/kg to about 5-10 mg/kg, or from about 7.5-15 mg/kg to about 12.5-20 mg/kg.

In some embodiments, the growth factor can be administered in an amount of about 0.2 μM-2 μM of the subject, or from about 0.2 μM-0.5 μM to about 0.25 μM-0.75 μM, or from about 0.5 μM-1 μM to about 0.75 μM-1.25 μM, or from about 1-1.5 μM to about 1.25 μM-2 μM.

While the bioactive wound dressing may be used for any type of wound, it may be especially suitable for use for chronic wounds, such as diabetic wounds. The dressing can be used in treatment methods for wound healing to provide an effective treatment for chronic, non-healing wounds. An example of the bioactive wound dressing uses silk as the matrix material, but the matrix material can be adapted to other natural or synthetic fibers, polymers, or the like. The immunomodulatory agent, preferably as a small molecule, such as histamines, can be used, and can be applied before, simultaneously, and/or sequentially with the dressing. Also, a growth factor in addition to the immunomodulator agent can result in enhanced wound healing when delivered before (pre-treatment composition), simultaneously (e.g., embedded in the dressing) or as a sequential treatment after application of the wound dressing (e.g., applied on the dressing for trans-dressing delivery or injected through the dressing or injected into skin surrounding the dressing).

In some embodiments, the bioactive dressing provides protection and local delivery of immunomodulator agents and growth factors. The dressing can be a resorbable, polymeric wound dressing that can significantly accelerate wound healing in cases of acute and diabetic slow-healing wounds. In some aspects, the wound treatment includes a combination of a polymeric wound dressing with a bioactive or immunomodulator molecule. The mode of delivery of the immunomodulator molecule can be a bolus delivery (e.g., in standard carrier such as water) or sustained delivery (e.g., in gel or paste matrix or in a particle). The timing of the delivery of the bioactive or immunomodulatory molecule can be at during different phases of wound healing, such as before, during and/or after application of the dressing to the wound. Additionally, optional delivery of a growth factor (e.g., associated with nanoparticle) can be along with the bioactive dressing, or before, during and/or after application of the dressing to the wound. The timing of delivery after application of the dressing can be varied as needed for the immunomodulator and/or growth factor.

The present bioactive wound dressing and immunomodulator agent can be used for any tissue opening, whether from surgery, injury or other, for any cut tear, wound, defect or the like. The present bioactive wound dressing and immunomodulator can be used on any tissue whether external (e.g., skin) or internal (e.g., organ, such as liver, colon, lung, muscle, blood vessel, stomach, or the like).

The bioactive wound dressing and immunomodulator agent can provide an improvement over other wound closure techniques and materials or at least provide suitable wound closure. The bioactive wound dressing and immunomodulator agent may be used with or without sutures, staples, clamps and/or tissue glues (e.g., cyanoacrylate based glues, such as Dermabond™ (topical skin adhesive)). Preferably, the bioactive wound dressing and immunomodulator agent can be used without sutures, staples, clamps and/or tissue glues.

In some embodiments, the present technology can also include the use of a laser to facilitate wound healing. Lasers are known to be used in wound healing and can be used with the bioactive dressing. While any suitable laser can be used, a near IR laser (e.g., IR-A), such as from about 700 nm to 1400 nm may be advantageously used. Also, other lasers, such as about 600 nm may also be used when used along with a light absorbing material either at the wound interface (e.g., between wound and dressing) or within the dressing. In some aspects, the treatment includes the combination of the bioactive dressing, immunomodulatory agent, and laser (e.g., without the growth factor). In some aspects, the treatment includes the combination of the bioactive dressing, immunomodulatory agent, growth factor, and laser. However, some embodiments may specifically exclude the use of a laser with the bioactive wound dressing and immunomodulatory agent.

In some embodiments, the present technology may use a chromophore composition having a chromophore that absorbs laser light, such as the wavelength of the laser used in some of the embodiments described herein. The chromophore composition can be a separate composition or included with the bioactive dressing, immunomodulatory agent composition, and/or growth factor composition. The chromophore composition allows for the methods of treatment to include the use of laser light.

In some embodiments, a light absorbing material can also be placed into a tissue opening (e.g., cut, tear, wound, defect, or other) and then radiated with light so as to absorb the light (e.g., laser light) and increase the temperature to a temperature that is sufficient to cause the material to interact with the tissue so as to close the opening in the tissue so as to approximate the tissue.

While the light absorbing material can absorb any type of light to increase the temperature thereof, laser light can be preferred. Additionally, laser-activated tissue sealing is known, and thereby the light absorbing material can be used in laser tissue sealing where the laser can be absorbed by the light absorbing material to cause a temperature increase. The laser light energy can be used to increase the temperature of the light absorbing material and the tissue interface surfaces in contact with the light absorbing material. Thereby, the light absorbing material when irradiated with a laser can facilitate tissue fusion with the light absorbing material and facilitate tissue-tissue fusion in areas around the light absorbing material.

Traditionally, light-absorbing chromophores and nanoparticles (e.g. gold nanorods) have been employed for converting near infrared (NIR) laser light to heat, resulting in the photothermal fusion of the sealant biomaterial with soft tissues.

In some instances, the wound dressing (e.g., polymer) can be the light absorbing material. It has been found that a light absorbing material, such as the natural polymers, semi-natural polymers or synthetic polymers with or without a crosslinker, such as the light absorbing materials described herein, that absorbs light, whether infrared, visible or ultraviolet, can be used.

In some embodiments, the wound dressing includes a laser stimulated material that responds to laser light of the near IR wavelengths. In some aspects, the laser stimulated material is stimulated by near IR laser light of about 700 nm to about 1400 nm, or about 800 nm. In one aspect, the laser stimulus responsive material is coated, embedded, crosslinked, or otherwise associated with the structural material of the wound dressing. In one aspect, the laser stimulus responsive material is in a particle form, such as when the stimulus responsive particle is a nanoparticle (e.g., nanosphere, nanorod, etc.). In one aspect, the structural material is shaped as a patch, bandage, sheet, or the like.

In one example, the laser stimulus responsive nanoparticles can be responsive to photothermal excitation in order to provide an additional benefit of enhancing wound closure. The stimulus responsive nanoparticles can convert light into heat, such as by plasmon resonance or other phenomena. This allows the wound dressing to be used conventionally, and to be treated with a stimulus (e.g., photothermal excitation—laser) to enhance wound closure and healing.

In one embodiment, the wound dressing is composed of a biocompatible material (e.g., polymer) that has nanoparticles (e.g., inorganic) that are sensitive to a laser stimulus. The biocompatible material of the wound dressing can be a structural material that provides the structure of the dressing, such as to form a bandage or a covering. The nanoparticles can provide the laser stimulus sensitivity to the dressing. The nanoparticles can be on the surface of the dressing, embedded in the structural material, retained in the structural material with the ability to translocate therein, fixed in the structural material in discrete locations, or otherwise included with the structural material. The nanoparticles can be encapsulated within a network of the structural material or can be crosslinked with the structural material. The nanoparticles may covalently bond with the structural material or be otherwise associated therewith.

In one embodiment, the nanoparticles (e.g., gold) can convert incident light (wavelength: 650-1350 nm) energy to heat by plasmon resonance, or collective oscillation of free electrons in the nanoparticle. The generated heat, upon reaching a critical temperature (e.g., 50-70° C.), can result in protein structural changes in the tissue.

Examples of materials that can be responsive to an optical (e.g., light) stimulus can include: gold nanorods, gold nanoparticles, gold nanospheres, indocyanin green, neodymium-doped nanoparticles (Nd:NPs), carbon nanotubes (CNTs), organic nanoparticles (O:NPs), gold nanostars (GNSs), or near-infrared absorbing dyes (absorbance of the dye between 650-1350 nm). Many materials have a range of wavelengths to which they are responsive, and may be tuned to a specific wavelength. In some aspects, the growth factor and/or immunomodulatory agent can be coated on these materials.

In some embodiments, the structural material includes a stimulus responsive material that is a photoresponsive material that is stimulated by light, wherein the stimulus responsive material is selected from gold nanorods, gold nanoparticles, gold nanospheres, gold nanostars, indocyanin green, neodymium-doped nanoparticles, carbon nanotubes, organic nanoparticles, or near-infrared absorbing dyes having absorbance between 650-1350 nm, and combinations thereof.

In some embodiments, the wound dressings can be functionalized with, or coated in, components such as antibiotics to inhibit bacterial growth or release specific MMP inhibitors (e.g., polyvinylpyrrolidone (PVP), doxycycline, Cefoxitin, broad spectrum antibiotics, etc.) to reduce anastomotic leakage or anti-inflammatory drugs (e.g., aceclofenac, acemetacin, aspirin, celecoxib, dexibuprofen, dexketoprofen, diclofenac, etodolac, etoricoxib, fenoprofen, flurbiprofen, ibuprofen, indometacin, ketoprofen, mefenamic acid, meloxicam, nabumetone, naproxen, sulindac, tenoxicam, and tiaprofenic acid) that can reduce the biological processes working to weaken the wound.

In some embodiments, the wound dressing composition is: Structural material is silk fibroin (extracted from Bombyx mori); Small molecule is histamine; and Growth factor nanoparticles are SDF1-ELP (stroll cell derived factor 1-elastin like polypeptide) and FGF2-ELP (basic fibroblast growth factor-elastin like polypeptide). The structural material can be 8 wt % silk fibroin or other biocompatible material may range from +/-1%, 2%, 3%, 4%, 5%, 6%, 7%, 8%, 9%, 10%, 15%, 20%, 25%, or greater than 8 wt %. Some examples include ranges from 6-10 wt %, 5-12 wt %, 4-15 wt %, 3-20 wt %, or 2-25 wt % of the biocompatible material. The amount of histamine (or alternative) and/or growth factor can vary as needed or desired.

In some embodiments, the bioactive dressing can be configured as a cover for a topical composition having the immunomodulatory agent. As such, a kit can be provided that includes the bioactive dressing separate from a topical composition having the immunomodulatory agent with or without the growth factor. This allows the topical composition to be applied to the wound surface and then covered by the bioactive dressing. In some aspects, the kit can include the growth factor as a sperate composition or as part of the composition containing the immunomodulatory agent. The separate growth factor composition and/or a composition having the immunomodulatory agent can be configured to be a trans-dressing composition that provides for the growth factor and/or immunomodulatory agent to diffuse across the dressing to the wound surface. Alternatively, the separate growth factor composition and/or a composition having the immunomodulatory agent can be configured as a needle injectable or other injectable composition to be injected through the wound dressing into or onto the wound or injected through skin adjacent or around the dressing.

In some embodiments, a wound dressing kit can include: a structural material formed into a dressing; an immunomodulatory agent composition; and a growth factor composition. In some embodiments, a wound dressing kit can include: a structural material formed into a dressing; and an immunomodulatory agent composition. In some embodiments, a wound dressing kit can include a structural material having the immunomodulatory agent and a separate growth factor composition. Instructions can be provided to administer the growth factor composition at a time after application of the wound dressing.

In some embodiments, a kit can also include a bioactive wound dressing having the immunomodulatory agent embedded therein for diffusion to the wound. In some aspects, the kit can also include a bioactive wound dressing having the growth factor embedded therein for diffusion to the wound. In some aspects, the kit can also include a bioactive wound dressing having the immunomodulatory agent and growth factor embedded therein for diffusion to the wound.

In some embodiments, a dressing cover can also be included in the kit to cover the top of the dressing after application to the skin, such as after application to a trans-dressing composition or after injection of a composition across the dressing to the wound. The dressing cover can be a temporary covering that is detachable from the dressing and may be a second dressing or of a material that inhibits diffusion of the immunomodulatory agent or growth factor across the cover so that they preferentially diffuse across the dressing. The dressing cover can be any suitable substrate material, ranging from a bandage to an adherent film (e.g., polyethylene, etc.), which is not significantly permeable to fluids under ambient conditions. The cover can be porous to oxygen or air under ambient conditions. In some aspects, the dressing cover can be configured as a transdermal device having an adhesive layer and backing, optionally with internal layers which can include the immunomodulatory agent and/or growth factor in a internal material or within the adhesive. This allows the bandage to have the same actives as the wound dressing composition, and can be used therewith.

In some embodiments, a method of treating a wound in a tissue can include: providing a wound dressing of one of the embodiments; applying the immunomodulatory agent (e.g., histamine) to the wound; applying the wound dressing into a wound in a tissue; and allowing the wound to heal with the immunomodulatory agent and wound dressing. In some aspects, the method can include applying the immunomodulatory agent to the wound before applying the wound dressing into the wound. In some aspects, the method can include applying the immunomodulatory agent to the wound at the same time as applying the wound dressing into the wound. In some aspects, the method can include applying the wound dressing into the wound so as to provide the immunomodulatory agent therefrom, such as a drug eluting dressing.

In some embodiments, the method can include irradiating the wound through the wound dressing or along an edge or end of the wound dressing with at least one laser light having a wavelength of about 700 nm to about 1400 nm, or about 800 nm. This can include irradiating the wound so as to cause a light absorbing material, such as the wound dressing, to increase in temperature. The method can include modulating power of the laser to modulate the temperature increase from the light, adjusting the laser power, or terminating the power.

In some embodiments, the method is devoid of using a suture, staple, clamp, or other structural element with the wound dressing. Accordingly, the dressing is used without these structural elements.

In some embodiments, however, the method can include using a suture, staple, clamp, or other structural element with the wound dressing to fasten the wound dressing to the tissue.

In some embodiments, the wound is selected from a cut, tear, surface area wound, skin defect, or combination thereof.

In some embodiments, the wound dressing includes the histamine and application of the wound dressing applies the histamine to the wound. In some aspects, the histamine is in a separate composition from the wound dressing, wherein the histamine composition is applied to the wound before applying the wound dressing to the wound. In some aspects, the histamine composition to at least one surface of the wound dressing. In some aspects, the method includes applying the histamine through the wound dressing to the wound.

In some embodiments, the method includes applying a growth factor to the wound. In some aspects, the method can include applying the growth factor to the wound before applying the wound dressing into the wound. In some aspects, the method can include applying the growth factor to the wound at the same time as applying the wound dressing into the wound. In some aspects, the method can include applying the wound dressing into the wound so as to provide the growth factor therefrom, such as a drug eluting dressing. In some aspects, the method includes applying the growth factor at a defined time period after application of the dressing, such as at least 6 hours later, at least 12 hours later, at least 18 hours later, at least 1 day later, at least 2 days later, at least 3 days layer, at least 4 days later, at least 5 days later, or at least 6 days later or longer. In some aspects, the wound dressing includes the growth factor and application of the wound dressing applies the growth factor to the wound. In some aspects, the growth factor is in a separate composition from the wound dressing, wherein the growth factor composition is applied to the wound before applying the wound dressing to the wound. In some aspects, the method includes applying the growth factor through the wound dressing, such as injecting through the material into or around the tissue having the wound.

In some embodiments, the method can include: removing the wound dressing (e.g., biostable) from the wound; and applying a second wound dressing (e.g., biostable when removable, or biodegradable when leaving in the wound) to the wound. The method can include optionally applying a second immunomodulatory agent (e.g., histamine) composition and/or second growth factor composition to the wound prior to or at the same time as applying the second wound dressing. The second application of growth factor can be at a time period after application of the second wound dressing. In some aspects, the first wound dressing integrates with the wound and a second wound dressing is applied thereover.

In some embodiments, the methods can include applying a second immunomodulatory agent (e.g., histamine) composition and/or growth factor composition to the wound without removing the wound dressing. The composition can be injected across the dressing into the tissue of the wound.

In some embodiments, the subject having the wound in the tissue has diabetes. As such, the treatment can be for a diabetic wound, such as a skin wound.

In some embodiments, the method can include affixing the wound dressing to tissue around the wound. In some aspects, the method can include adhering the wound dressing to the tissue with an adhesive (e.g., pressure sensitive adhesive, PSA), which can be provided on or added to a wound-facing surface of the wound dressing.

In some embodiments, the method can treat a wound with a size that is about 1 mm to about 100 mm, about 2 mm to about 75 mm, about 3 mm to about 50 mm, about 4 mm to about 25 mm, about 5 mm to about 10 mm.

EXAMPLES

The present technology has been shown to provide local delivery of histamine (e.g., an immune modulator) in combination with a silk dressing film (e.g., silk fibroin with embedded gold nanorods) so as to result in faster closure of acute and slow healing diabetic wounds when compared to a conventional wound dressing (e.g., Tegaderm™ (transparent film dressing)). The data provided herein shows that immunocompetent BALB/c mice served as a model for acute wounds, while genetically diabetic BKS.Cg-Dock7m+/+Leprdb/J (db/db) mice were utilized as a model for slow healing diabetic wounds. The histamine composition was applied topically on 5-millimeter mid-dorsal full thickness wounds and covered with either Tegaderm™ (transparent film dressing) or a silk dressing and irradiated with 800 nm near infrared laser (NIR) light. Significant reduction in wound area and improved tissue biomechanical recovery was observed in histamine treated wounds.

As shown in the data, the bioactive wound dressings were tested in a full-thickness punch biopsy in vivo mice model (e.g., immunocompetent healthy mice model for acute wounds and immunocompetent diabetic mice model for diabetic slow healing wounds). After wounding and application of bioactive wound dressing, the wound bed was irradiated with an 800 nm near-infrared (NIR) laser for 2 minutes and the wound bed surface temperature never exceeded 60-65° C. during the irradiation. Post-wounding, the mice were recovered for 7-11 days and their healing kinetics were monitored for different treatment groups. Significant reduction in wound area and improved tissue biomechanical recovery was observed in histamine treated wounds. Silk dressing-histamine treated wounds showed complete wound closure and higher tissue strength compared to Tegaderm™-histamine (transparent film dressing) treated wounds at day 7 post-wounding in acute wounds (n=10) and 11 (n=4) days in diabetic wounds. It was found that adding SDF1-ELP growth factor as a simultaneous or sequential treatment further accelerated wound closure and resulted in higher skin strength recovery (n=4 for acute and diabetic wounds).

An example protocol is as follows. Full-thickness punch biopsy dorsal wounds were created on mice, bioactive wound dressing applied, and the wounds were splinted to prevent wound closure by contraction. Either immunomodulator molecule was delivered on the day of wounding or a later time-point to accelerate wound healing. Significant reduction in wound area and improved tissue biomechanical recovery was observed in histamine treated wounds. Silk dressing-histamine treated wounds showed complete wound closure and higher tissue strength compared to Tegaderm™- histamine (transparent film dressing) treated wounds at day 7 post-wounding in acute wounds (n=10) and 11 (n=4) days in diabetic wounds.

These findings demonstrate that bioactive silk dressings are a promising treatment option for enhancing wound healing and that they outperform clinically approved polyurethane wound dressing.

FIG. 1 includes images of a wound closure procedure, which was performed with BALB/c mice (about 8-10 weeks old), with a wound size of about 5 mm (n=10), and with a histamine concentration of 3.4 mg/kg per mouse. As shown, the silk dressing with histamine and laser treatment provide the best result, followed by silk and saline with laser being about the same as Tegaderm™ (transparent film dressing) with histamine and laser treatment, which were all better than Tegaderm™ (transparent film dressing) and saline with laser treatment.

Figure 2:
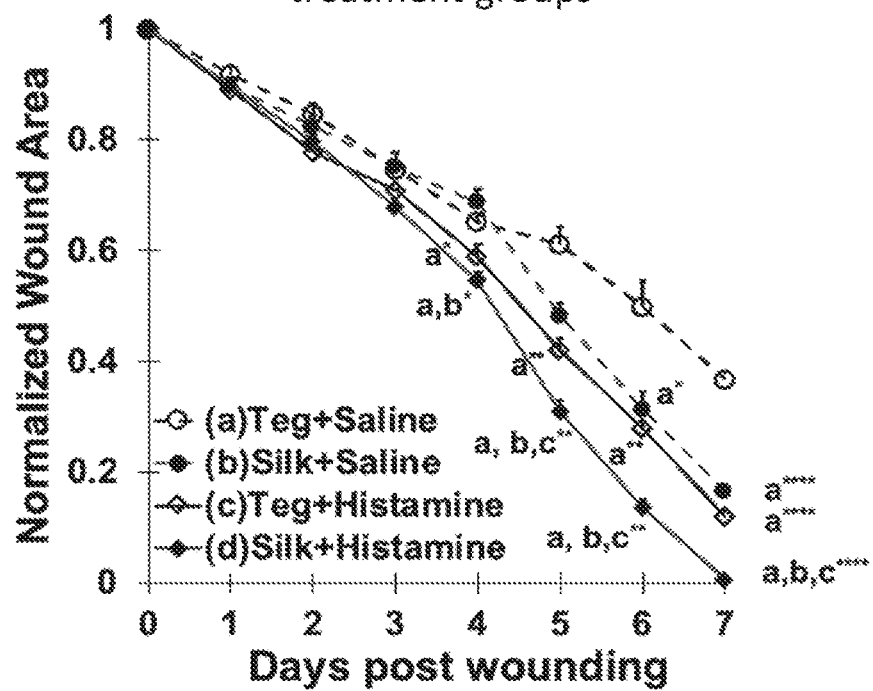
FIG. 2 includes a graph of the normalized wound area versus the days post wounding over 7 days post treatment with different treatment compositions.

FIG. 2 shows data for the normalized wound area over a 7-day period for different treatments as listed. The silk and histamine treatment provided superior results. The data is provided for wound closure kinetics that shows Tegaderm™ (transparent film dressing) and saline versus silk and saline, which is a control without histamine, for an acute wound healing BALB/c mice. The data shows Tegaderm™ (transparent film dressing) and histamine (H2) versus silk and histamine (H2), where the silk performs better than Tegaderm™ (transparent film dressing) when both are used with histamine.

Figure 3:
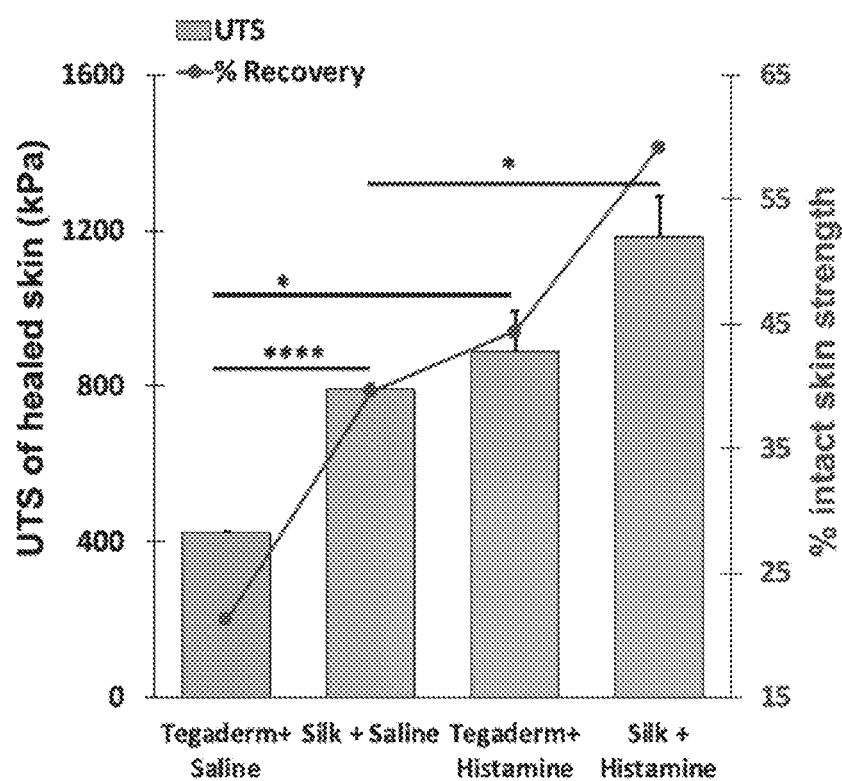
FIG. 3 includes a graph that shows the ultimate tensile strength (UTS, kPa) for the percentage of intact skin strength.

FIG. 3 includes a graph that shows the ultimate tensile strength (UTS, kPa) for the percentage of intact skin strength. The data shows the silk and histamine treatment outperforms the Tegaderm™ (transparent film dressing) and histamine combination, the silk and saline combination, and the Tegaderm™ (transparent film dressing) and saline combination.

Additional data showed the IL-1β fold change relative to saline treatment for silk and histamine compared to Tegaderm™ (transparent film dressing) and histamine, where the silk histamine has enhanced early production of IL-1β, showing the immunomodulatory activity. This shows increased pro-inflammatory cytokines in serum.

Additional data showed the IL-1β fold change relative to saline treatment for silk and histamine compared to Tegaderm™ (transparent film dressing) and histamine, where the silk histamine has enhanced early production of IL-1β, showing the immunomodulatory activity. This shows increased pro-inflammatory cytokines in serum.

Additional data for the acute wound model shows that silk and histamine provide superior a-SMA activation, superior CD31 activation, and superior epidermal thickness. H1 indicates data for the histamine receptor H1, and H2 indicates data for the histamine receptor H2. The data shows that histamine improves reduction of the dermal gap of a wound, provides higher neovascularization, higher contractile activity, higher re-epithelialization and better solution of inflammation. In all cases, silk with histamine outperforms Tegaderm™ (transparent film dressing) with histamine. The histamine provides higher skin strength recovery and resolution of inflammation.

Figure 4:
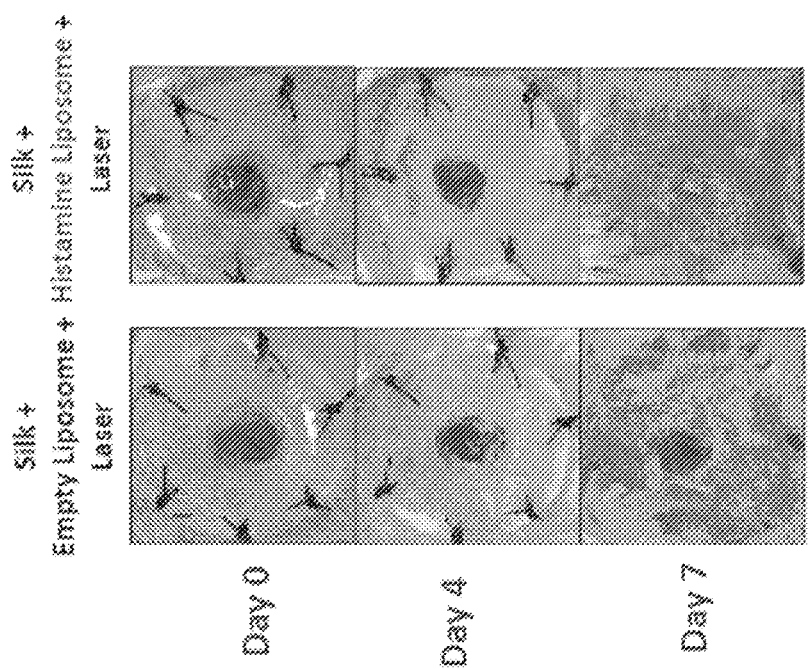
FIG. 4 includes images that show results when the histamine is in a liposome and treated with a laser.

FIG. 4 includes images that show results when the histamine is in a liposome and treated with a laser, which is clearly an improvement over no histamine in the liposomes.

Figure 5:
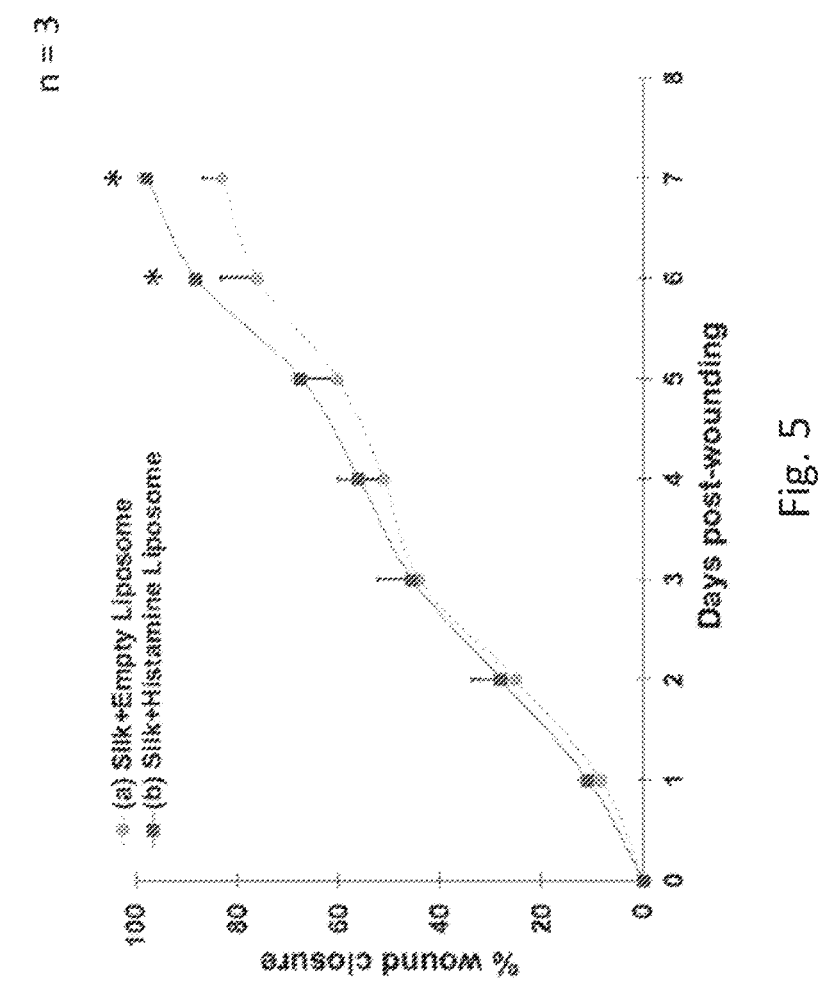
FIG. 5 includes a graph that shows the wound closure percentage versus days post-wounding.

FIG. 5 includes a graph that shows the wound closure percentage versus days post-wounding. Here, the histamine liposome is significantly better than no histamine in the liposome.

Figure 6A:
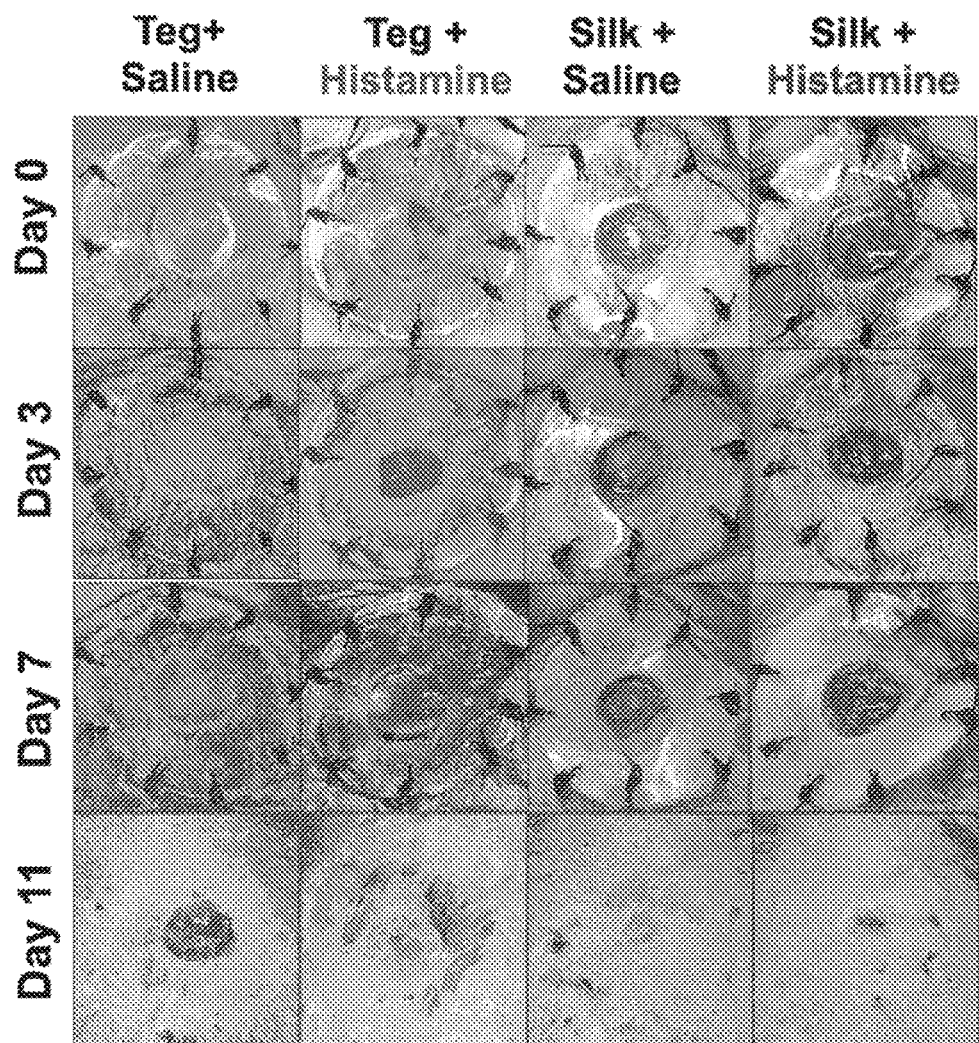
FIG. 6A includes images that show results for a diabetic wound healing model with the Tegaderm™ (transparent film dressing) and silk dressings with and without histamine.

FIG. 6A includes images that show results for a diabetic wound healing model with the Tegaderm™ (transparent film dressing) and silk dressings with and without histamine. The experiments were with BDS.Cg-Dock7m+/+Leprdb/J mice (about 10 weeks old), with a wound size of 5 mm (n–4), and a histamine concentration of 3.4 mg/kg per mouse. Here, the silk and histamine performed the best.

Figure 6B:
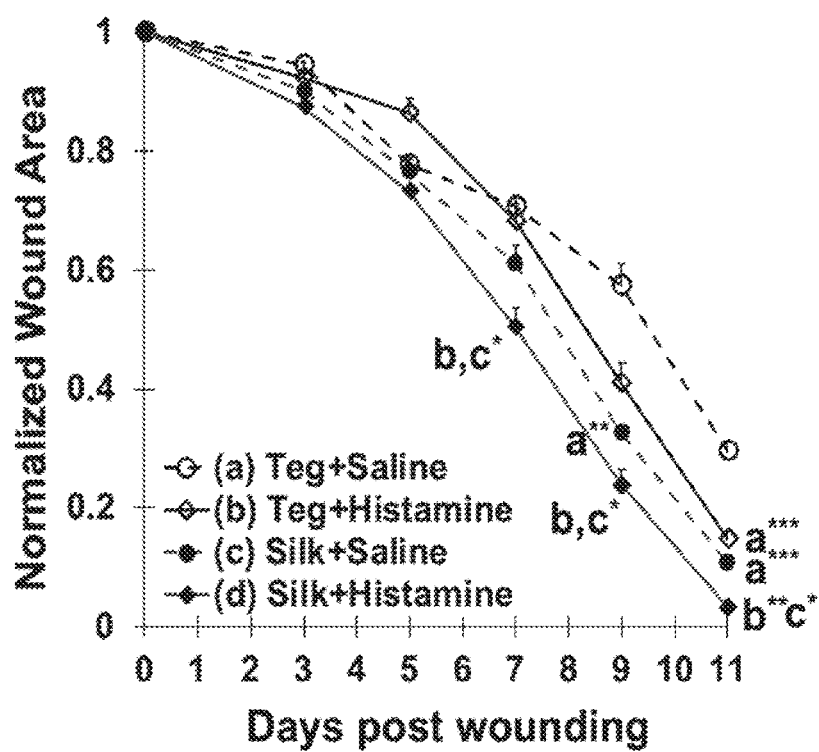
FIG. 6B includes a graph of the normalized wound area versus days post wounding.

FIG. 6B includes a graph of the normalized wound area versus days post wounding, which shows the silk and histamine performed the best followed by silk without histamine, followed by Tegaderm™ (transparent film dressing) and histamine. The combination of silk and histamine resulted in complete wound closure in 11 days.

Figure 6C:
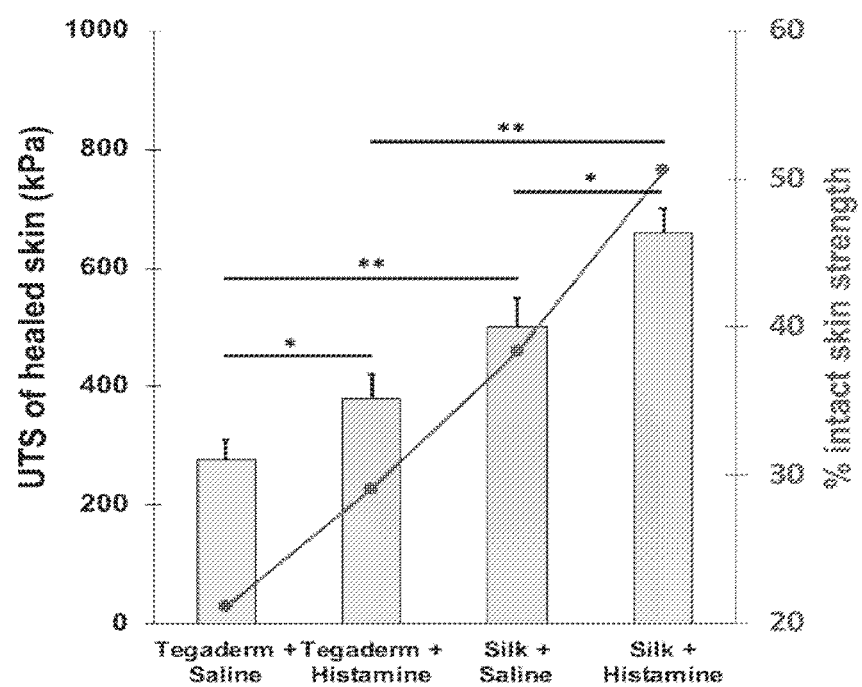
FIG. 6C includes a graph that shows the ultimate tensile strength (UTS, kPa) for the percentage of intact skin strength.

FIG. 6C includes a graph of the ultimate tensile strength (UTS) for different treatments, which shows the silk and histamine performed the best followed by silk without histamine, followed by Tegaderm™ (transparent film dressing) and histamine. The combination of silk and histamine resulted in the highest UTS (bars) and percent of intact skin strength (line).

Figure 7:
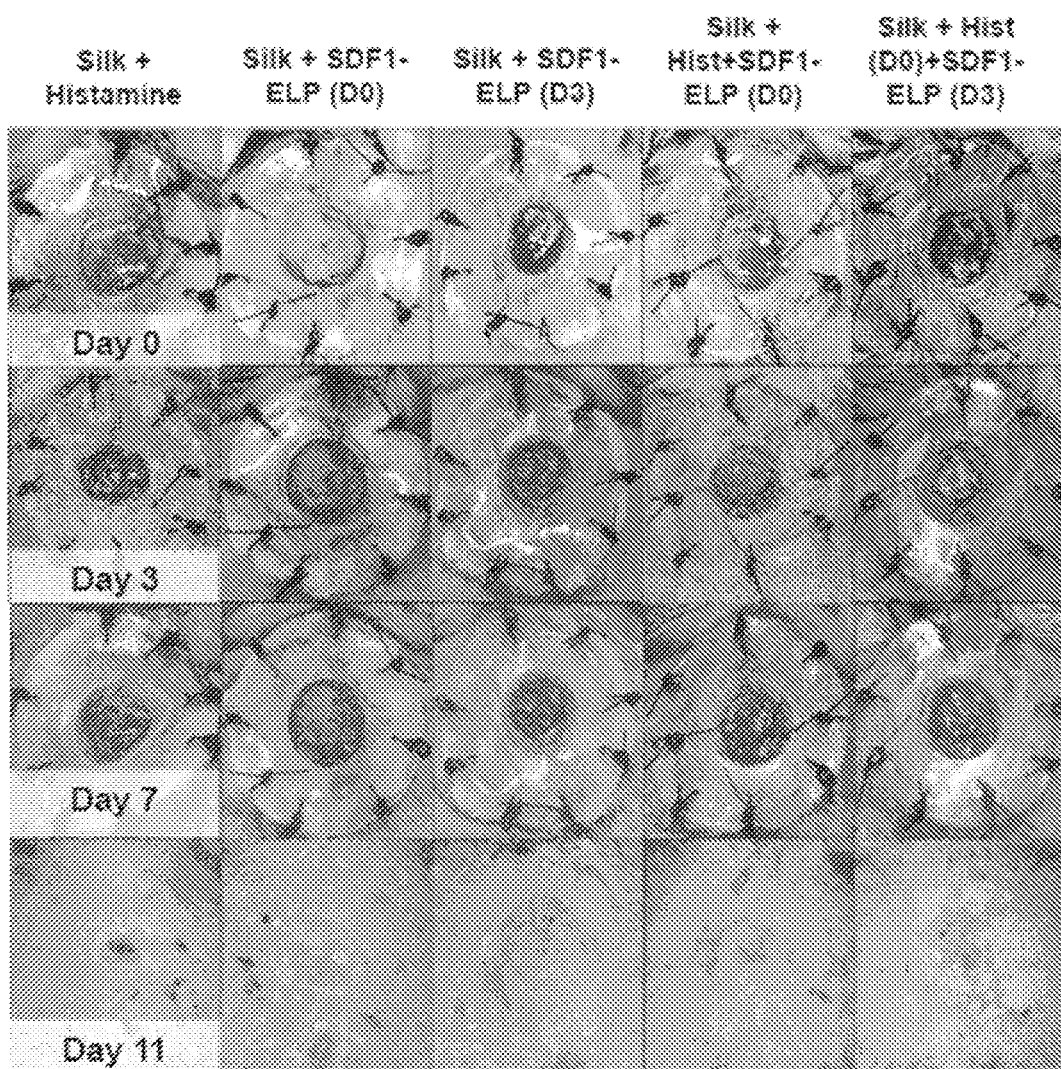
FIG. 7 includes images that show results for the diabetic would healing model using silk plus histamine, silk plus growth factor SDF1-ELP (fusion peptide) on day 0 (D0), silk plus growth factor SDF1-ELP (fusion peptide) on day 3 (D3), silk and histamine plus growth factor SDF1-ELP (fusion peptide) on day 0 (D0); and silk and histamine plus growth factor SDF1-ELP (fusion peptide) on day 0 (D0).

FIG. 7 includes images that show results for the diabetic would healing model using silk plus histamine, silk plus growth factor SDF1-ELP (fusion peptide) on day 0 (D0), silk plus growth factor SDF1-ELP (fusion peptide) on day 3 (D3), silk and histamine plus growth factor SDF1-ELP (fusion peptide) on day 0 (D0); and silk and histamine plus growth factor SDF1-ELP (fusion peptide) on day 0 (D0). As shown, adding growth factor SDF1-ELP initially (at day 0) or at day 3 significantly improved the skin strength recovery and healing. Additional data shows the UTS (kPa) of healed skin for the different combinations plus the addition of growth factor (SDF1-ELP). The data shows that the addition of growth factor improved the response over histamine in silk.

Also, additional data shows the improvement when adding growth factor SDF1-ELP initially (at day 0) or at day 3 significantly improved the skin strength recovery and healing. Here, the skin is shown to heal faster with the silk, histamine, and growth factor.

Figure 8:
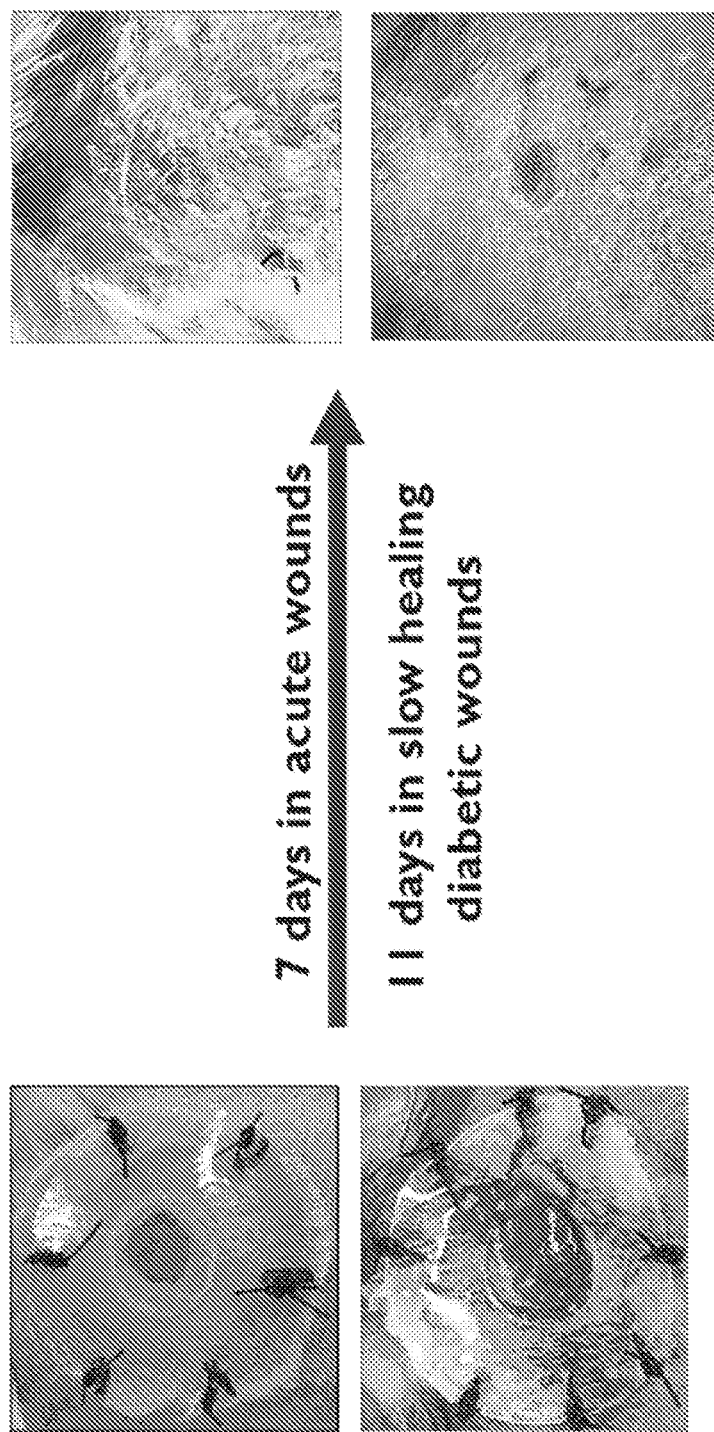
FIG. 8 shows examples of the silk-GNR (silk gold nanorod) dressing with histamine is useful for wound healing.

FIG. 8 shows examples of the silk-GNR (silk gold nanorod) dressing with histamine is useful for wound healing. The examples show closure in 7 days for an acute wound, and 11 days for a slow healing diabetic wound.

The temporal delivery of growth factor nanoparticles (GFNPs) in slow healing diabetic wounds (db/db mice) was studied. Experiments tested the delivery of a therapeutic (GFNPs) in a temporal manner for an influence in wound repair efficacy and be whether the therapeutic is beneficial for healing. These studies were performed in db/db mice (slow healing diabetic wounds), 5 mm wounds, histamine concentration was 3.4 mg/kg and GFNPs concentration was 2 µM, respectively. We have performed these studies with two different GFNPs; SDF1-ELP and bFGF-ELP, wherein ELP is an elastin-like polypeptide.

Figure 9A:
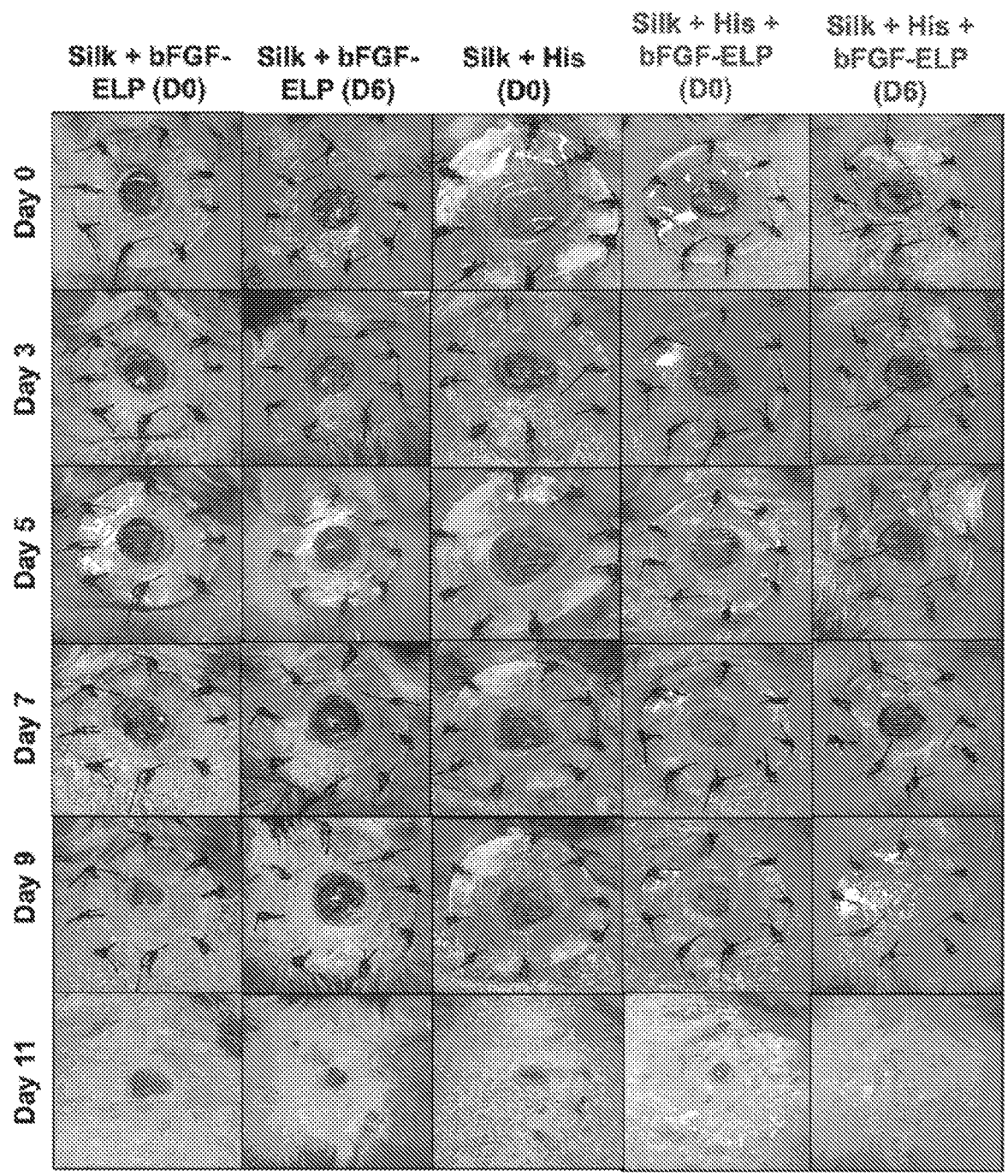
FIG. 9A shows a matrix of the days versus the treatment composition and day.

In an example, we delivered histamine and GFNPs in the following manner (FIG. 9A): Histamine and GFNPs along with silk fibroin on Day 0 post wounding; and Histamine along with silk fibroin on Day 0 post wounding+second dose of GFNPs on Day 6 post wounding delivered using subcutaneous injection. FIG. 9A shows a matrix of the days versus the treatment composition and day.

Figure 9B:
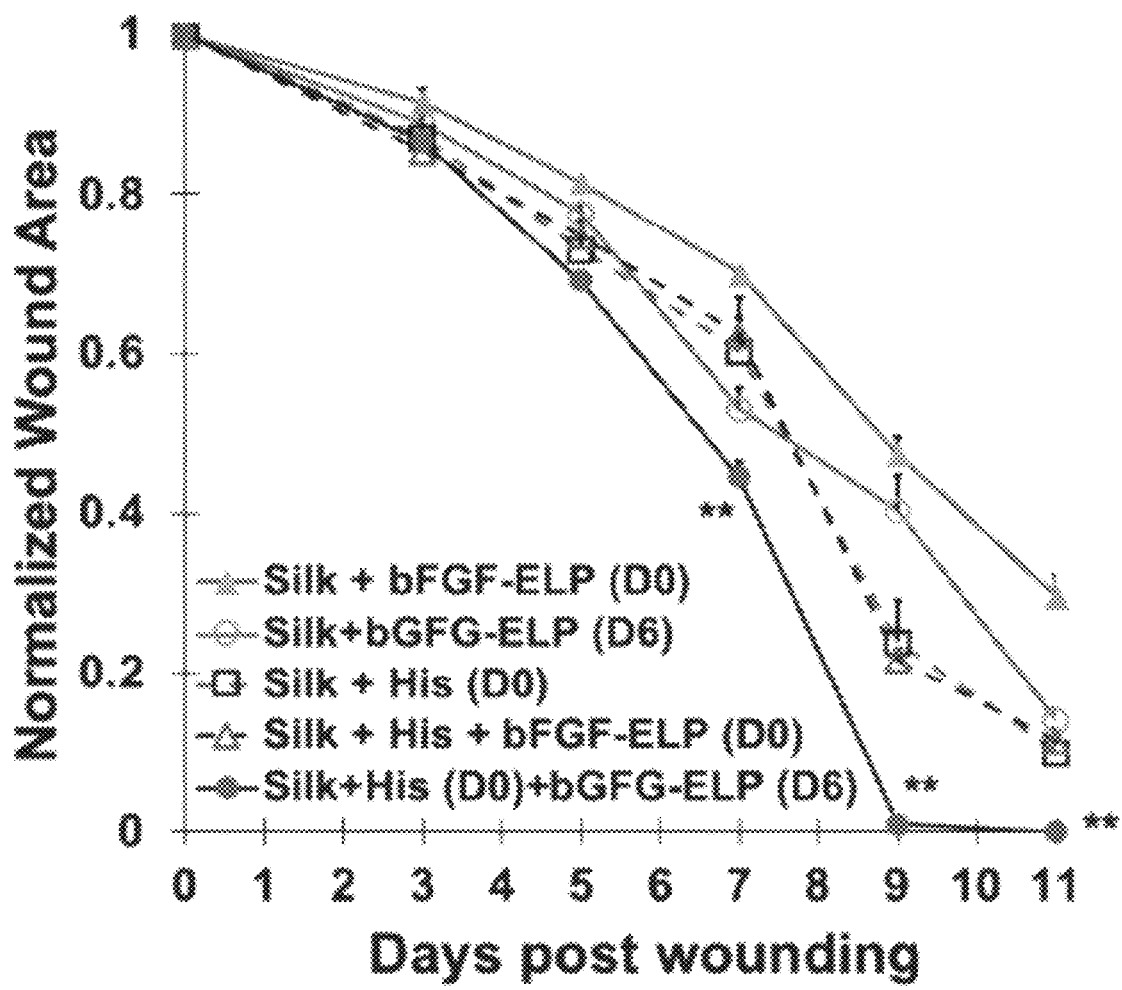
FIG. 9B includes a graph that shows the normalized wound area versus the days post wounding for different treatments.
Figure 9C:
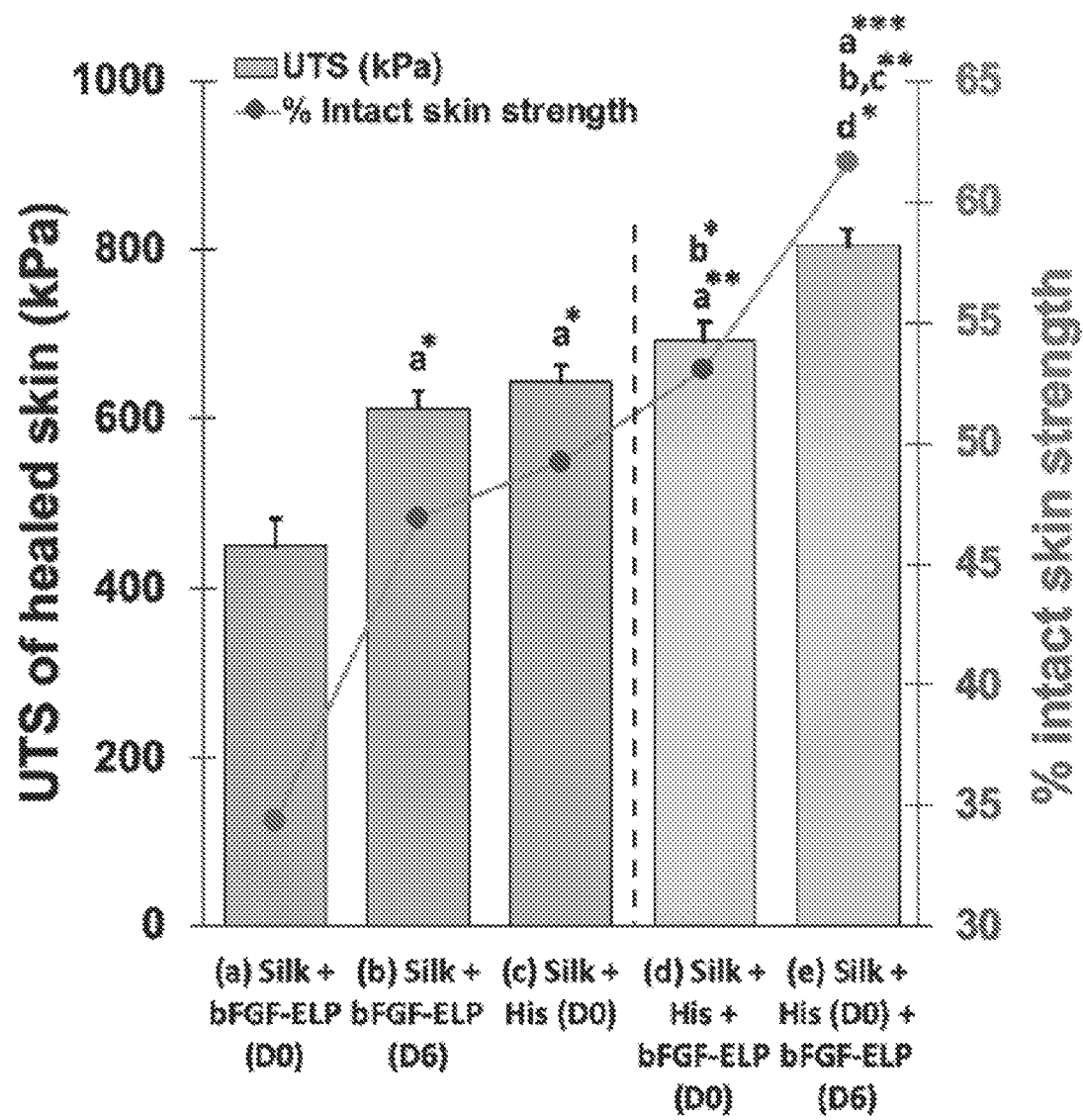
FIG. 9C includes a graph that shows the UTS (kPa) of healed skin for the different treatments.

When compared with treatment with single agents (either histamine or GFNPs), histamine+GFNPs combination treatment resulted in accelerated wound closure (FIG. 9B) and also significantly improved healed skin strength (FIG. 9C). Post histamine treatment on Day 0, GFNPs delivered on Day 6 post wounding resulted in accelerated wound closure and improved healed skin strength compared to GFNPs delivered on Day 0 along with histamine itself (FIGS. 9B, 9C). This shows temporal modulation of the second therapeutic delivery does have an effect of efficacy of wound healing.

We also tested whether the timing of the second therapeutic mattered, hence importance of temporal modulation based on different phases of wound healing to further improve healing efficacy. These studies were performed in db/db mice (slow healing diabetic wounds), 5 mm wounds, histamine concentration was 3.4 mg/kg and GFNPs concentration was 2 µM, respectively. We have performed these studies with two different GFNPs; SDF1-ELP and bFGF-ELP. We delivered combination of histamine and GFNPs in the following manner—Histamine and GFNPs along with silk fibroin on Day 0 post wounding; Histamine along with silk fibroin on Day 0 post wounding +second dose of GFNPs on Day 3 post wounding delivered using subcutaneous injection; and Histamine along with silk fibroin on Day 0 post wounding+second dose of GFNPs on Day 6 post wounding delivered using subcutaneous injection.

Figure 9D:
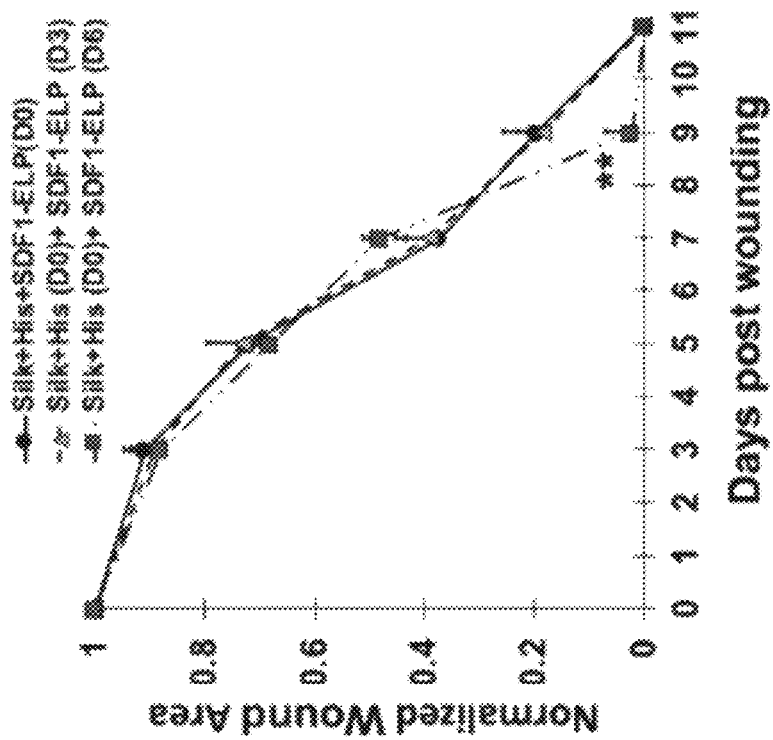
FIG. 9D includes a graph that shows the normalized wound area versus days post wounding for different treatments.
Figure 9D:
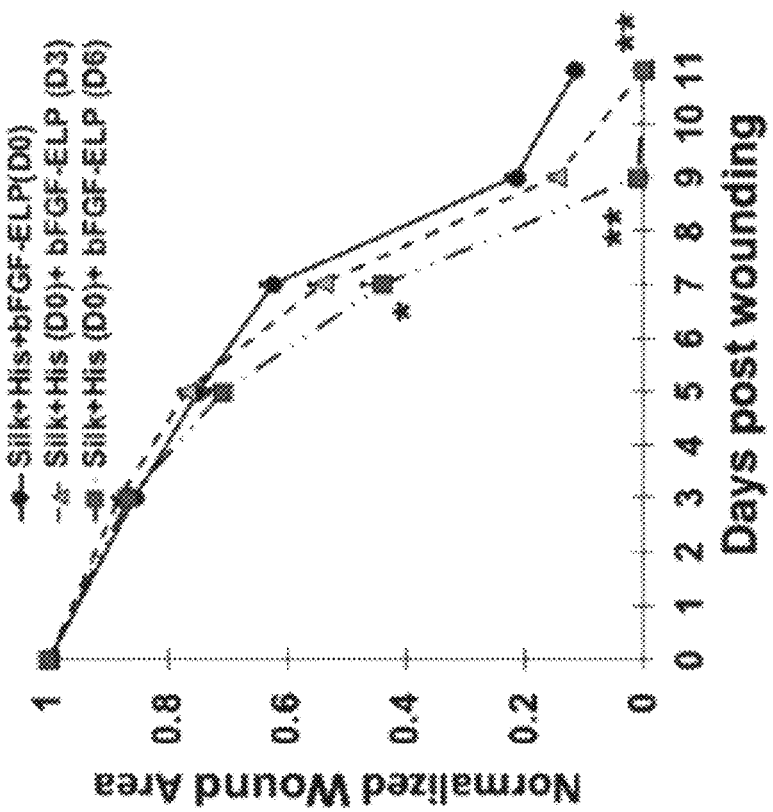
Figure 9E:
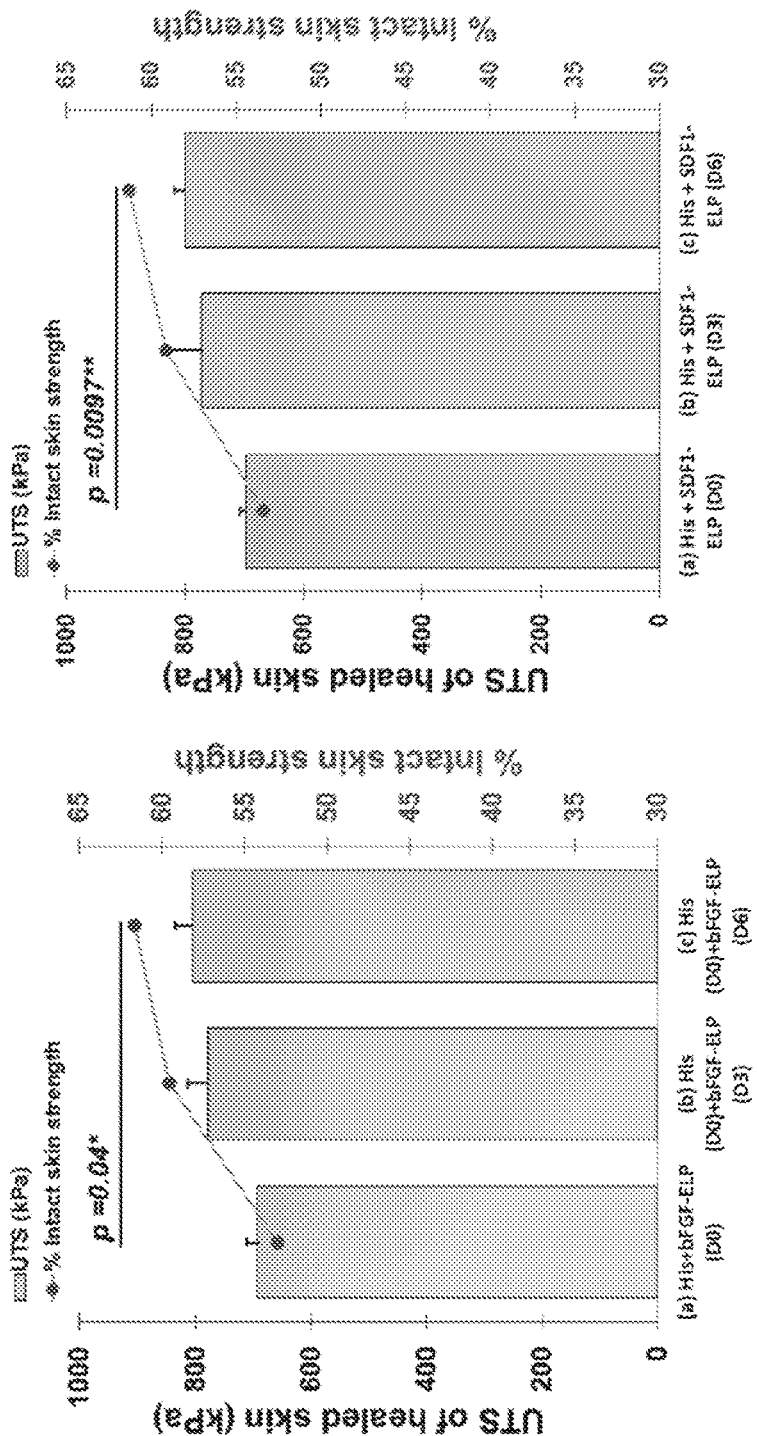
FIG. 9E includes a graph that shows the UTS (kPa) of healed skin compared to the percent intact skin strength for different treatments for different days.

Compared to simultaneous delivery on Day 0 and sequential delivery on Day3, sequential delivery on Day 6 did help in closing wounds significantly earlier (complete closure 2 days prior to other groups) (FIG. 9D) and also resulted in significantly higher healed skin strength (FIG. 9E). Similar beneficial effects were observed with SDF1-ELP as well as bFGF-ELP. These results show us that timing the delivery of GFNPs right at the transition of inflammatory to proliferative phases of wound healing was the best delivery condition compared to delivery either immediately after wounding or somewhere within the inflammatory phase.

Additionally, Elastin-Like Polypeptide (ELP) was used alone as a control. We tested whether ELP in itself influenced healing efficacy. These studies were performed in BALB/c mice (acute wounds), 5 mm wounds, ELP concentration 2 µM (per wound/mouse). Histamine and GFNPs concentration were 3.4 mg/kg and 2 µM, respectively. Histamine and GFNPs concentration were same as previous reported studies. The GFNPs used in this study is SDF1-ELP.

Figure 10A:
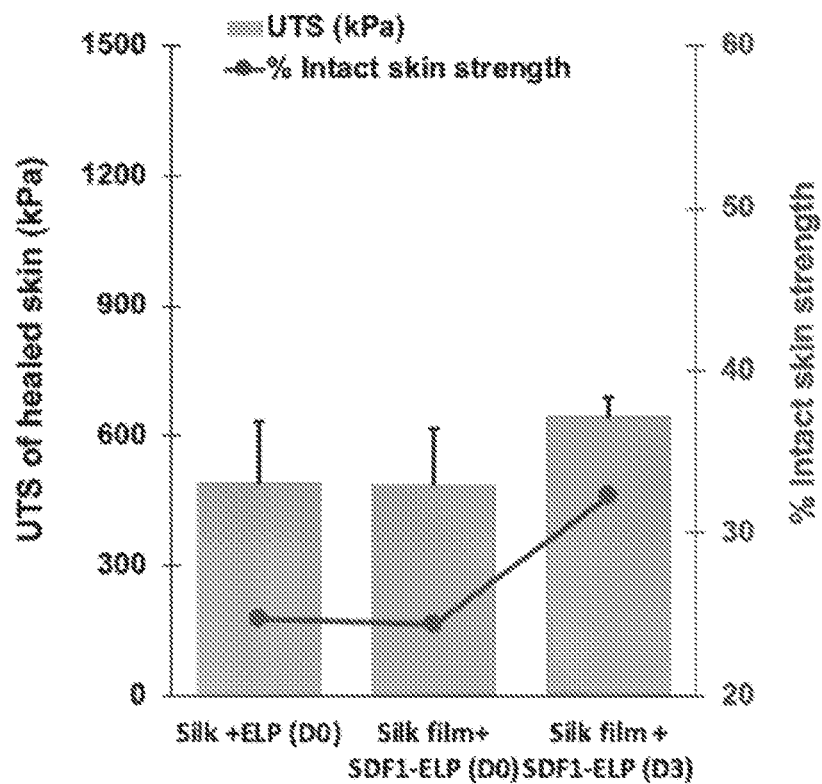
FIG. 10A includes a graph that shows the UTS (kPa) of healed skin compared to the percent intact skin strength for different treatments with ELP on different days.
Figure 10B:
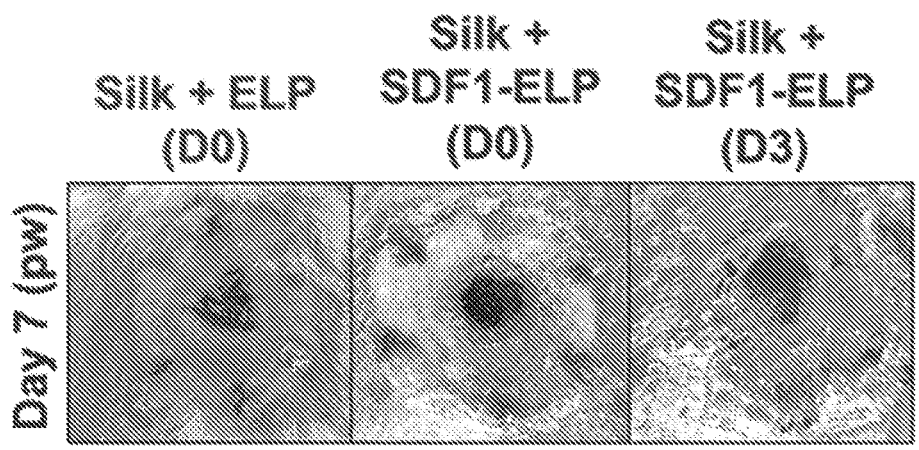
FIG. 10B includes images that show the healed skin for different treatments with
ELP on different days.
Figure 10C:
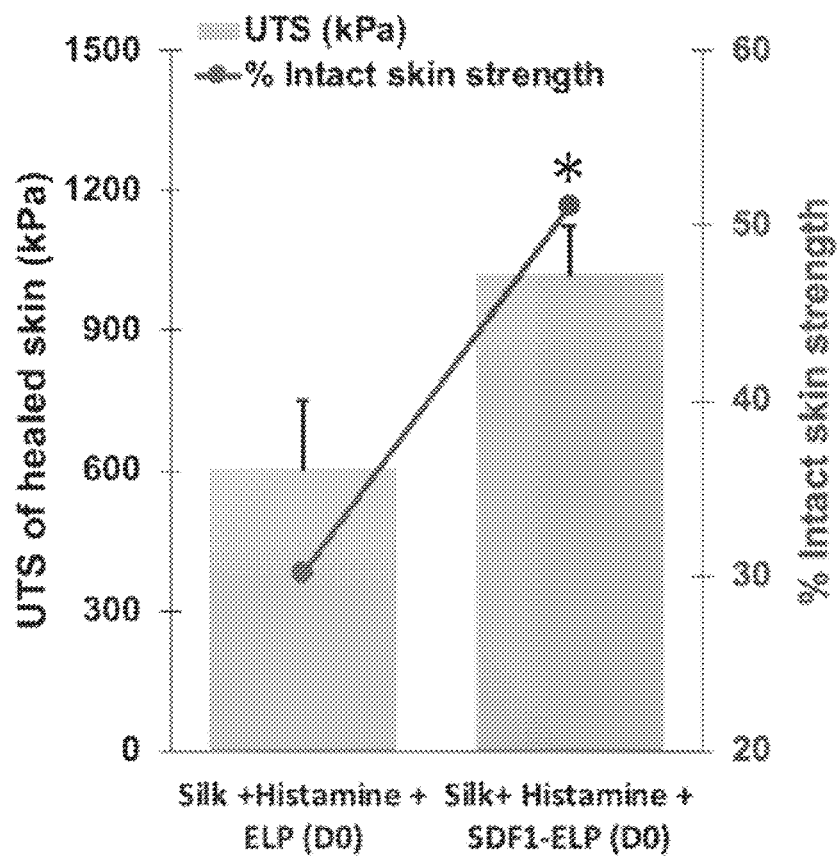
FIG. 10C includes a graph that shows the UTS (kPa) of healed skin compared to the percent intact skin strength for different treatments with ELP with or without histamine FIG. 10D includes a graph that shows healed skin for different treatments with ELP with or without histamine.
Figure 10D:
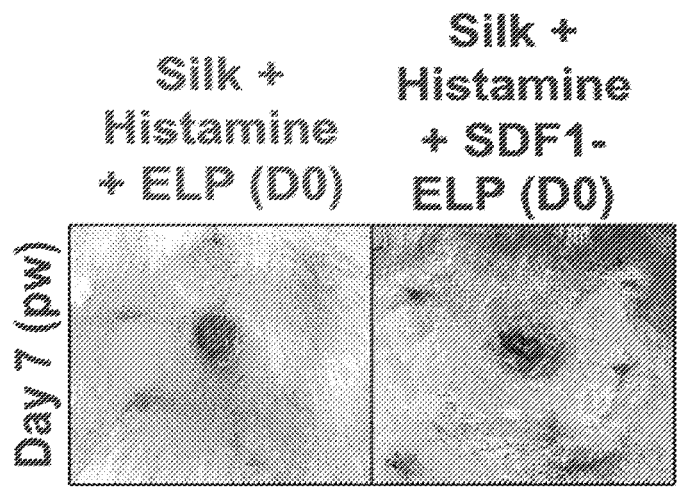

We delivered ELP along with silk fibroin dressing on Day 0 and compared it to the delivery of SDF1-ELP and silk fibroin on Day 0 or 3. Our results showed that ELP alone did not significantly increase strength of healed skin (FIG. 10A graph and FIG. 10B images). When compared with co-delivery of histamine, SDF1-ELP and histamine combination resulted in significantly higher healed skin strength compared to histamine and ELP combination (p-value=0.047). This result shows us ELP alone does not influence healing (FIG. 10C graph and FIG. 10D images).

Figure 11B:
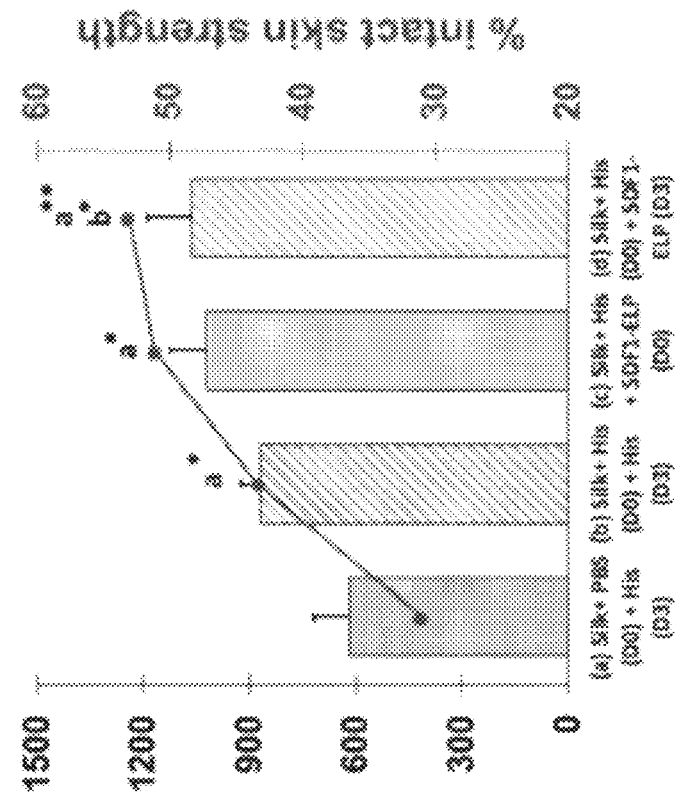
FIG. 11B includes a graph that shows the UTS (kPa) of healed skin compared to the percent intact skin strength for different treatment sequences.
Figure 11A:
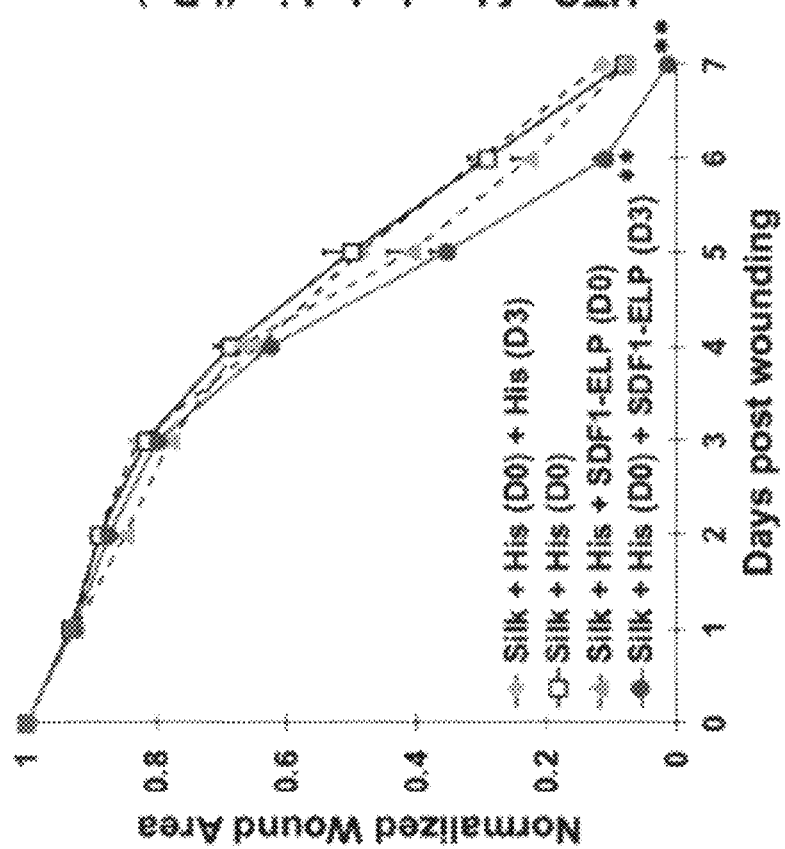
FIG. 11A include a graph that shows the normalized wound area versus days post wounding for different treatment sequences.

A histamine double dosage control (e.g., two sequential dosage of histamine) was investigated. We tested whether a double dosage, such as two sequential doses, of histamine (e.g., first dose of Day 0 post wounding and second dose on Day 3) in itself has similar or better efficacy in closing wounds compared to simultaneous and sequential treatment of histamine and GFNPs. These studies were performed in BALB/c mice (acute wounds) and in 5 mm wounds. Histamine and GFNPs concentration were 3.4 mg/kg and 2 µM, respectively. Histamine and GFNPs concentration were same as previous reported studies. The GFNPs used in this study is SDF1-ELP. We delivered histamine in the following manner—Histamine along with silk fibroin dressing on Day 0 post wounding (like previous studies); Histamine delivered on Day 3 post wounding. Wounds were treated with PBS and silk fibroin film alone on Day 0; Histamine along with silk fibroin on Day 0 post wounding+second dose of histamine on Day 3 post wounding delivered using subcutaneous injection; and Histamine along with silk fibroin on Day 0 post wounding+GFNPs delivered sequentially on Day 3 post wounding. When compared with a double dose of histamine in a sequential manner, histamine+GFNPs treatment in a sequential manner (histamine on Day 0 and GFNPs on Day 3) significantly improved wound closure (FIG. 11A) and healed skin strength (FIG. 11B). These results showed us that temporal delivery of histamine and GFNPs is beneficial compared to double dosage of histamine.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A wound dressing comprising:
   a structural material formed into a dressing, wherein the structural material ranges from about 2-25 wt %;
   at least one immunomodulatory agent associated with the dressing; and
   a growth factor associated with the dressing;
   wherein the wound dressing comprises gold particles in the structural material; and;
   wherein the growth factor is associated with the gold particles.

2. The wound dressing of claim 1, wherein the structural material is biodegradable and/or bioabsorbable.

3. The wound dressing of claim 1, wherein the structural material is a natural substance or a natural substance that has been chemically modified.

4. The wound dressing of claim 1, wherein the structural material is a synthetic substance.

5. The wound dressing of claim 1, wherein the immunomodulatory agent is selected from the group consisting of histamine, histamine receptor agonists, MCP1, antibodies, 2-pyridylethylamine, histamine-trifluoromethyl-toluidine dimaleate (HTMT), diphenhydramine, terfenadine, dimaprit, cimetidine, ranitidine, Nα-methylhistamine, azomethine prodrug of (R)-α-methylhistamine, impentamine, clobenpropit, immepip, imetit, 4-Methylhistamine and combinations thereof.

6. The wound dressing of claim 1, wherein the growth factor is selected from the group consisting of stromal cell-derived factor (SDF1), basic fibroblast growth factor (bFGF), transforming growth factor (TGF), epidermal growth factor (EGF), keratinocyte growth factor (KGF), vascular endothelial growth factor (VEGF), heat shock protein 90 alpha (HSP90α), F5 subunit of heat shock protein 90 alpha (HSP90α), each optionally fused with elastin-like polypeptide (ELP), and combinations thereof.

7. The wound dressing of claim 1, further comprising the structural material including a laser stimulated material that is stimulated by near IR laser light of about 650 nm to about 1400 nm.

8. A wound dressing kit comprising:
   a structural material formed into a wound dressing;
   wherein the structural material ranges from about 2-25 wt %;
   at least one immunomodulatory agent associated with the dressing; and
   a growth factor associated with the dressing;
   wherein the wound dressing comprises gold particles in the structural material; and;
   wherein the growth factor is associated with the gold particles.

9. A method of treating a wound in a tissue comprising:
   applying to the wound a first wound dressing comprising:
   a structural material formed into a dressing,
   wherein the structural material ranges from about 2-25 wt %;
   at least one immunomodulatory agent associated with the dressing; and
   a growth factor associated with the dressing;
   wherein the wound dressing comprises gold particles in the structural material; and;
   wherein the growth factor is associated with the gold particles.

10. The method of claim 9, further comprising:
    irradiating the wound through the first wound dressing with at least one laser light having a wavelength of about 700 nm to about 1400 nm, or about 800 nm.

11. The method of claim 9, wherein the method is devoid of using a suture, staple, clamp, or other structural element with the first wound dressing to treat the wound.

12. The method of claim 9, further comprising using a suture, staple, clamp, or other structural element with the first wound dressing to fasten the wound dressing to the tissue.

13. The method of claim 9, further comprising:
removing the first wound dressing from the wound; and
applying a second wound dressing to the wound with or without applying a second administration of immunomodulatory agent and/or growth factor.

14. The method of claim 9, further comprising applying a second immunomodulatory agent and/or growth factor composition to the wound without removing the first wound dressing from the wound.

15. The method of claim 9, wherein a subject having the wound in the tissue has diabetes.

* * * * *